United States Patent [19]

Goers et al.

[11] Patent Number: 4,867,973

[45] Date of Patent: * Sep. 19, 1989

[54] ANTIBODY-THERAPEUTIC AGENT CONJUGATES

[75] Inventors: John W. F. Goers, Atascadero, Calif.; Hurley D. King, Yardley, Pa.; Chyi Lee, New Brunswick; Daniel J. Coughlin, Plainsboro, both of N.J.; Vernon L. Alvarez, Morrisville, Pa.; John D. Rodwell, Yardley, Pa.; Thomas J. McKearn, New Hope, Pa.

[73] Assignee: Cytogen Corporation, Princeton, N.J.

[*] Notice: The portion of the term of this patent subsequent to Jun. 9, 2004 has been disclaimed.

[21] Appl. No.: 650,375

[22] Filed: Sep. 13, 1984

Related U.S. Application Data

[63] Continuation-in-part of Ser. No. 646,328, Aug. 31, 1984, and Ser. No. 646,327, Aug. 31, 1984, each is a continuation-in-part of Ser. No. 442,050, Nov. 16, 1982, abandoned, which is a continuation-in-part of Ser. No. 356,315, Mar. 9, 1982, Pat. No. 4,671,958.

[51] Int. Cl.$^4$ .................... A61K 39/00; A61K 37/00; A23J 37/00

[52] U.S. Cl. .................... 424/85.91; 424/85.8; 424/86; 424/87; 530/387; 530/388; 530/389; 530/390; 530/391; 530/828; 514/2; 514/6; 514/8

[58] Field of Search ............... 530/387, 388, 389, 390, 530/391, 828; 514/2, 68; 424/85, 86, 87; 427/85.91, 85.8

[56] References Cited

U.S. PATENT DOCUMENTS

| | | | |
|---|---|---|---|
| 3,970,521 | 7/1976 | Zaborsky et al. | 195/63 |
| 4,093,607 | 6/1978 | Sela et al. | 260/112 B |
| 4,167,449 | 9/1979 | Gargiulo et al. | 435/16 |
| 4,217,338 | 8/1980 | Ouash | 424/1 |
| 4,256,833 | 3/1981 | Ali et al. | 435/7 |
| 4,263,279 | 4/1981 | Sela et al. | 424/85 |
| 4,287,345 | 9/1981 | Kotani et al. | 546/261 |
| 4,419,444 | 12/1983 | Ouash | 435/7 |
| 4,671,958 | 6/1987 | Rodwell et al. | 421/85 |

FOREIGN PATENT DOCUMENTS

| | | |
|---|---|---|
| 154520 | 12/1977 | Japan . |
| 155094 | 12/1979 | Japan . |
| 1446536 | 2/1975 | United Kingdom . |
| 2015530 | 9/1979 | United Kingdom . |

OTHER PUBLICATIONS

Monsigny et al, *FEBS Letters*, vol. 119 (1), Sep. 1980, pp. 181–186, "Preparation and Biological Properties of a Covalent Antitumor Drug–Arm–Carrier", CDAC Conjugate).

Trovet et al., *Proc Natl Acad Sci*, Jan. 1982, vol. 79, pp. 626–629, "A Covalent Linkage Between Davnorubicon and Proteins That is Stable in Serum and Reversible by Lysosumal Protease as Required for a Lysosomotropol Drug–Carrier Conjugate: In Vitro and In Vivo Studies".

Paul, *Fundamental Immunology*, 1984, pp. 132, 149.

March, *Advanced Organic Chemistry*, 2nd Ed, 1972, pp. 824–827.

Anderson and Parrish, Science 220: 524–527 (1983).

Bale et al., Cancer Research 40: 2965–2972 (1980).

Bing, Biochemistry 8: 4503–4510 (1969).

Blythman et al, Nature 290: 145–146 (1981).

Bunton, in Oxidation in Organic Chemistry, vol. I, Widberg, ed., Academic Press, New York, p. 365 (1965).

Caporale et al., J. Immunol. 126: 1963–1965 (1981).

Cooper, Biochemistry 14: 4245–4251 (1975).

Cooper et al., J. Biol. Chem. 234: 445–448 (1959).

Davis and Preston, Science 213: 1358–1388 (1981).

(List continued on next page.)

Primary Examiner—Robin L. Teskin
Attorney, Agent, or Firm—Pennie & Edmonds

[57] ABSTRACT

This invention relates to antibody-therapeutic agent conjugates having a therapeutic agent covalently attached to an antibody or antibody fragment. Also described are methods for intermediates in the preparation of antibody conjugates. Therapeutic in vivo methods utilizing such antibody-therapeutic agent conjugates are described.

79 Claims, No Drawings

OTHER PUBLICATIONS

Dougherty et al., in Porphyrin Photosensitization, Kessel and Dougherty eds., Plenum Publishing Corp., New York, (1983) pp. 3–13.
Ghose et al., J. Natl. Cancer Inst. 61(3): 657–676 (1978).
Gregoriadis, Pharmac. Ther. 10: 103–118 (1980).
Gregoriadis, Nature 265: 407–411 (1977).
Heath et al., Biochim Biophys. Acta. 640: 66–81 (1981).
Huang et al., J. Biol. Chem. 255(17): 8015–8018 (1980).
Hurwitz et al., Int. J. Cancer 24: 461–470 (1979).
Jackson, "Periodic Acid Oxidations" in Organic Reactions, vol. 2, pp. 341–375 (1944).
Jentoft and Dearborn, J. Biol. Chem. 254: 4359–4365 (1979).
Lesserman et al., Nature 288: 602–604 (1980).
March, in Advanced Organic Chemistry: Reactions, Mechanisms and Structures, McGraw Hill Co., New York, pp. 824–825 (1978).
Martin et al., Biochem 20: 4229–4238 (1981).
Mew et al., J. Immunol. 130: 1473–1477 (1983).
Mitra and Lawton, J. Amer. Chem. Soc. 101: 3097–3110 (1979).
Murayama et al., Immunochem. 15: 523–528 (1978).
Parrish, J. Investig. Dermatol. 77: 45–50 (1981).
Reid and Porter, Ann. Rev. Biochem 50: 433–464 (1981).
Rowland, in Targeted Drugs, Goldberg ed., Interscience Publications, New York, pp. 57–72 (1983).
Sim et al., Biochem. J. 163: 219–227 (1977).
Stanworth and Turner, in Handbook of Experimental Immunology, vol. I, 2d ed. Weir, ed. Blackwell Scientific Publications, London, Chapter 10 (1973).
Willan et al., FEBS Lett. 80: 133–136 (1977).

ANTIBODY-THERAPEUTIC AGENT CONJUGATES

CROSS-REFERENCE TO RELATED APPLICATIONS

This application is a continuation-in-part of application Ser. Nos. 646,328 and 646,327, both filed Aug. 31, 1984, which in turn are continuations-in-part of application Ser. No. 442,050, filed Nov. 16, 1982, now abandoned, which in turn is a continuation-in-part of application Ser. No. 356,315, filed Mar. 9, 1982 now U.S. Pat. No. 4,671,958.

TABLE OF CONTENTS

1. FIELD OF THE INVENTION
2. BACKGROUND OF THE INVENTION
   2.1. CARRIER SYSTEMS
   2.2. COVALENT ATTACHMENT TO ANTIBODIES
   2.3. CARRIER SYSTEMS USING MONOCLONAL ANTIBODIES
   2.4. PHOTORADIATION THERAPY
3. SUMMARY OF THE INVENTION
4. BRIEF DESCRIPTION OF THE FIGURES
5. DETAILED DESCRIPTION OF THE INVENTION
   5.1. ANTIBODIES
   5.2. METHODS FOR ATTACHING THERAPEUTIC AGENTS TO ANTIBODIES AND ANTIBODY FRAGMENTS
      5.2.1. ATTACHMENT TO OXIDIZED CARBOHYDRATE MOIETIES
         5.2.1.1. CHEMICAL METHODS OF OXIDATION
         5.2.1.2. ENZYMATIC METHODS OF OXIDATION
         5.2.1.3. PREPARATION OF ANTIBODY-THERAPEUTIC AGENT CONJUGATES
         5.2.1.4. STABILIZATION OF THE ANTIBODY CONJUGATES
      5.2.2. ATTACHMENT TO SULFHYDRYL GROUPS
   5.3. THERAPEUTIC AGENTS
   5.4. LINKERS
      5.4.1. BRANCHED LINKERS
      5.4.2. CLEAVABLE LINKERS
      5.4.3. SPACERS AND CLEAVABLE ELEMENTS
      5.4.4 SERUM COMPLEMENT AND SELECTION OF LINKERS
      5.4.5. LINKERS FOR RELEASE WITHOUT COMPLEMENT ACTIVATION
      5.4.6. NON-CLEAVABLE LINKERS OR DIRECT ATTACHMENT
         5.4.6.1. NON-CLEAVABLE LINKERS
         5.4.6.2 NON-CLEAVABLE CONJUGATES
   5.5. USES OF ANTIBODY-THERAPEUTIC AGENT CONJUGATES
      5.5.1. PHOTORADIATION THERAPY
      5.5.2. SUBSTRATE MODIFICATION
   5.6. ADVANTAGES OF ANTIBODY-THERAPEUTIC AGENT CONJUGATES
6. EXAMPLES: SERIES I
   6.1. OXIDATION OF MOUSE MONOCLONAL IgM
   6.2. ATTACHMENT OF LINKER TO EDDHA
   6.3. PREPARATION OF IgM-LINKER-EDDHA CONJUGATES
   6.4. CARBODIIMIDE ATTACHMENT OF LINKER-EDDHA TO IgM
   6.5. CARBODIIMIDE ATTACHMENT OF EDDHA TO IgM
   6.6. EFFECTS OF CARBOHYDRATE-MEDIATED ATTACHMENT TO ANTIBODIES
7. EXAMPLES SERIES II
   7.1. OXIDATION OF THE CARBOHYDRATE MOIETY OF THE ANTIBODY MOLECULE
   7.2. PREPARATION OF THE TRIPEPTIDE-AMC FOR ATTACHMENT TO THE ANTIBODY MOLECULE
   7.3. ATTACHMENT OF PHENYLHYDRAZINE TRIPEPTIDE-AMC TO THE OXIDIZED CARBOHYDRATE MOIETY OF THE ANTIBODY MOLECULE
8. EXAMPLES: SERIES III
   8.1 COMPLEMENT FIXATION ASSAYS
      8.1.1. PREPARATION OF HUMAN COMPLEMENT
      8.1.2. HEMOLYTIC ASSAY FOR COMPLEMENT FIXATION
      8.1.3. NON-HEMOLYTIC ASSAY FOR COMPLEMENT MEDIATED RELEASE OF AMC
9. EXAMPLES: SERIES IV
   9.1. CLEAVAGE OF THE TRIPEPTIDE-AMC BY TRYPSIN AND UROKINASE
   9.2. CLEAVAGE OF TRIPEPTIDE-AMC DERIVATIVES BY UROKINASE, TRYPSIN, PLASMIN AND PURIFIED COMPLEMENT COMPONENTS C4,2 AND C1S
   9.3. CLEAVAGE OF GLY-GLY-ARG-TYR* BY UROKINASE AND TRYPSIN
   9.4. CLEAVAGE OF A PLASMINOGEN ANALOG BY TRYPSIN AND UROKINASE
   9.5. CLEAVAGE OF A PURIFIED COMPLEMENT COMPONENT ANALOG
10. EXAMPLES: SERIES V
    10.1 FORMATION OF ANTIBODY-GLY-GLY-ARG-TYR*
    10.2. CLEAVAGE OF ANTIBODY-GLY-GLY-ARG-TYR* CONJUGATES BY TRYPSIN AND UROKINASE
    10.3. ATTACHMENT OF THE ANTIBODY-GLY-GLY-ARG-TYR* CONJUGATES TO CELLS AND ENZYMATIC CLEAVAGE
    10.4. FORMATION AND CLEAVAGE OF CELL-ANTIBODY GLY-GLY-ARG-AMC
11. EXAMPLES: PREPARATION OF PORPHYRIN DERIVATIVES
    11.1. PREPARATION OF DEUTEROPORPHYRIN DIHYDRAZIDE
    11.2. PREPARATION OF PROTOPORPHYRIN DIHYDRAZIDE
    11.3. PREPARATION OF HEMATOPORPHYRIN DIMETHYL ESTER
    11.4. PREPARATION OF HEMATOPORPHYRIN DIHYDRAZIDE
12. EXAMPLE: ATTACHMENT OF HEMATOPORPHYRIN DIHYDRAZIDE TO ANTIBODY
    12.1. PREPARATION OF ANTIBODY-HEMATOPORPHYRIN DIHYDRAZIDE CONJUGATES

12.2. CYTOTOXICITY ASSAY USING THE ANTIBODY-HEMATOPORPHYRIN DIHYDRAZIDE CONJUGATE

1. FIELD OF THE INVENTION

The present invention relates to the general area of antibody systems capable of delivering therapeutic agents to target sites in vivo. The therapeutic agents are covalently attached to antibodies or antibody fragments either through linkers or by direct attachment to form antibody conjugates. The antibody-therapeutic agent conjugates substantially retain the immunospecificity and immunoreactivity of the original antibody.

In a preferred embodiment the invention is directed to attachment of a therapeutic agent through a linker which may be either cleavable or non-cleavable. These antibody-therapeutic agent conjugates which comprise the therapeutic agent attached via the linker to the antibody molecule substantially retain the immunospecificity and immunoreactivity of the unconjugated antibody. Certain embodiments of the invention include attachment via linkers susceptible to cleavage by a proteolytic enzyme such that the resulting conjugate retains the ability to bind antigen and activate complement. The invention also includes attachment via linkers susceptible to cleavage by urokinase, plasmin, trypsin, a tissue plasminogen activator or other enzymes having proteolytic activity. In all of these embodiments cleavage of the linker promotes the release of the therapeutic agent in an active or activatable form at the target site.

Another preferred embodiment of the invention relates to attachment of certain therapeutic agents to an antibody molecule such that the resulting conjugate is delivered to a specific target site and the therapeutic agent is not released. The therapeutic agent may be activated at the target site.

Still another preferred embodiment relates to the attachment of an enzyme to an antibody molecule such that the resulting conjugate is delivered to a specific target site where the enzyme catalyzes reactions of therapeutic value.

The invention also relates to several methods for preparing such antibody-therapeutic agent conjugates, intermediates which are useful in preparing the conjugates, novel therapeutic agents, and methods for using such therapeutic agents.

2. BACKGROUND OF THE INVENTION

A variety of carrier molecules have been utilized with limited success in the delivery of therapeutic agents to a site of action. In practice the carrier should be non-toxic and target site specific. Ideally there should be a mechanism for maintenance or release of the active form of the therapeutic agent from the carrier at the target site.

2 1. CARRIER SYSTEMS

A number of agents have been utilized as carrier molecules with limited success in drug delivery systems. In practice the carrier should be non-toxic and target site specific. Ideally there should be a mechanism for release of the active form of the drug from the carrier at the target site. Carrier molecules such as DNA, liposomes, proteins, steroid hormones and antibodies (whole antibody molecules or fragments) have been used in conjunction with a broad spectrum of pharmaceutical or cytotoxic agents such as: radioactive compounds (e.g., $^{125}I, ^{131}I$); agents which bind DNA, for instance, alkylating agents or various antibiotics; antimetabolites such as methotrexate; agents which act on cell surfaces (e.g., venom phospholipases and microbial toxins); and protein synthesis inhibitors (e.g., diphtheria toxin and toxic plant proteins).

A number of investigators have reported target systems involving attachment of compounds or pharmaceutical agents directly to conventional antibodies, monoclonal antibodies, or to Fab portions of antibodies directed against tumor antigens. See Blythman et al., 1981, Nature 290:145-146; Davis and Preston, 1981, Science 213:1385-1388; Hurwitz et al., 1979, Int. J. Cancer 24:461-470; U.S. Patent No. 4,093,607; and U.K. Patent No. 1,446,536. Urdal and Hakomori (1980, J. Biol. Chem. 255(21):10509-10579) describe an antibody targeted, avidin mediated, drug killing of tumor cells.

Although antibody carrier systems can be highly specific for the target site, a significant problem exists in that the therapeutic agent may not be released at that site. If release is necessary, the antibody-drug conjugates must be internalized by the tumor cell. There, release would occur through cleavage by lysosomal enzymes. Additionally, the non-site specific linkage of the therapeutic agent to (random) sites on the antibody molecule may interfere with antigen binding capacity, thus reducing the effectiveness of the system.

2.2. COVALENT ATTACHMENT TO ANTIBODIES

A number of different reactions have been used to covalently attach compounds to antibodies. This has been accomplished by reaction of the amino acid residues of the antibody molecule, including the amine groups of lysine, the free carboxylic acid groups of glutamic and aspartic acid, the sulfhydryl groups of cysteine and the various moieties of the aromatic amino acids.

There are serious disadvantages to these methods of covalent attachment to the polypeptide backbone of an antibody molecule. The amino acid sequences of the light and heavy chains of immunoglobulins contain all of the amino acids relatively regularly and randomly dispersed throughout the molecule, including the antigen binding region. To the extent any chemical modification occurs in this antigen binding region, one has introduced a change in the recognition element of the antibody. Such changes would be expected to, and, in fact do, change the affinity and specificity of the antibody for antigen. In a population of different antibodies, such alteration in the antigen binding region results in complete inactivation of some antibodies and in lesser degrees of inactivation of others in relation to the proximity of the alterations to the antigen binding site. This inactivation may be due to a change within or very near the antigen binding site to alter the conformation of the binding site so as to make it unreactive, or may be due to a change in a region outside the antigen binding region so as to limit access of antigen to the antigen binding region. Methods involving amino acids which are relatively regularly and randomly dispersed throughout the antibody are referred to as non-site specific methods.

One of the most commonly used non-specific (random) methods of covalent attachment is the carbodiimide reaction to link a carboxy (or amino) group of a compound to amino (or carboxy) groups f the antibody. Additionally, bifunctional agents such as dialdehydes or imidoesters have been used to link the amino group of a compound to amino groups of the antibody molecule.

Some investigators have used the Schiff base reaction to link compounds to antibody molecules. This method involves the periodate oxidation of a drug or cytotoxic agent that contains glycol or hydroxy groups, thus forming an aldehyde which is then reacted with the antibody molecule. Attachment occurs via formation of a Schiff base with amino groups of the antibody molecule. Isothiocyanates have been used as coupling agents for covalently attaching compounds to antibodies. By this method fluorescent compounds have been attached to antibody molecules for use in fluorescence microscopy (Brandtzaeg, 1973, Scand. J. Immunol. 2:273-290) and cell sorting systems (Loken and Herzenberg, 1975, Annals N.Y. Acad. Sci. 254:163-171).

Interchain disulfide bonds can also be used as sites of covalent attachment. However, even if one is successful in selectively reducing only the interchain disulfide bonds, several functional properties of the antibody may be adversely affected, such as functional affinity, agglutination ability and the ability to fix complement.

2.3. CARRIER SYSTEMS USING MONOCLONAL ANTIBODIES

Monoclonal antibodies produced by the hybridoma technique of Kohler and Milstein (1975, Nature 256:495-497; 1976, Eur. J. Immunol. 6:511-519) or related techniques provide distinct advantages for use as carriers for delivery of therapeutic agents to a site of action. First, monoclonal antibodies bind to only one molecular site (i.e., an epitope) with specific binding constants. Second, such antibodies are homogeneous and thus are purified with relative ease. Third, monoclonal antibodies can be made in large quantities by particular hybridoma cell lines.

The discovery of tumor-produced or tumor-associated antigens has allowed the preparation of monoclonal antibodies which are immune-specific for solid tumors such as human colon, breast, hepatatoma, melanoma and germ cell tumors (see reviews by Carrasquillo et al., 1984, Cancer Treatment Repts. 68:317-328; Kennel et al., 1984, Bio. Sci. 34:150-156).

For example, Gilliland et al. have demonstrated the therepeutic feasibility of using anticolorectal monoclonal antibodies conjugated to diptheria toxin A (1980, Proc. Natl. Acad. Sci. U.S.A. 77:4539). In in vitro cytotoxic assays, nearly all of the carcinoma cells treated with this conjugate were killed.

2.4. PHOTORADIATION THERAPY

Advances in optics technology and greater understanding of photochemistry and photobiology have raised interest in the technique of photoradiation therapy for treating a variety of disease states. Photoradiation therapy using "hematoporphyrin derivative" (HpD) for photosensitization of tumor cells has been under development with some success for several years. Using HpD, patients have been treated for cancers such as primary and metastatic skin cancers, lung, trachea, esophagus, bladder, brain, eye cancers and internal metastasis in the peritoneal cavity.

When light of the appropriate wavelength interacts with HpD, a cytotoxic mediator (i.e., the singlet oxygen) initiates chemical reactions which destroy tumor cells. Indeed, HpD seems to be preferentially taken up and retained by many tumors compared to adjacent tissues (see Dougherty, In Porphyrin Photosensitization, New York: Plenum Publishing Corp., 1983, pp. 3-13). In many cases it is possible to produce a selective effect on the tumor by exposing the tumor and surrounding area to light of the appropriate wavelength using a laser. The laser output beam may be connected to optical fibers of the appropriate size and applied either directly into the tumor or externally to the general location of the tumor.

Despite promising developments, however, photochemicals (e.g., hematoporphyrin and other photosensitizers) have several disadvantages for clinical use. First, there is great potential for damage to normal tissue if the areas adjacent to the tumor are not protected. There must be precise timing between drug administration and light exposure. A second disadvantage is that patients receiving photoradiation therapy are generally extremely sensitive to sunlight and must avoid exposure to the sun, frequently for as long as four weeks. Third, the dosage levels of photosensitizer required for therapy are very high and may have a negative effect on normal tissue.

The ideal photosensitizer should be designed so that it has greater tumor specificity, requiring a lower therapeutic dose level, hence mitigating the deleterious effect of higher doses. Greater tumor specificity leads to more efficient localization to the site of action and less opportunity for dispersal throughout the body.

Mew et al. have demonstrated the use of monoclonal antibody conjugated via carbodiimide bonding to hematoporphyrin as an anti-cancer agent in vivo and in vitro (1983, J. Immunol. 130:1473-1477).

3. SUMMARY OF THE INVENTION

According to the general method of the present invention, a therapeutic agent is covalently attached to an antibody or antibody fragment. The covalent attachment of the therapeutic agent is accomplished so that the resulting antibody conjugate retains the ability to bind antigen. In particular, such methods include attachment to oxidized carbohydrate moieties of antibodies or antibody fragments, or to the sulfhydryl groups of reduced antibodies or reduced (Fab')$_2$ fragments.

In particular, the invention concerns methods for preparing antibody-therapeutic agent conjugates, comprising:

(a) reacting an antibody or antibody fragment with an oxidizing agent to form an aldehyde group in the carbohydrate moiety of the antibody or antibody fragment;

(b) reacting the aldehyde group of the resultant oxidized antibody or antibody fragment with an amine group of a linker, said linker containing an amine group selected from the group consisting of primary amine, secondary amine, hydrazine, hydrazide, hydroxylamine, phenylhydrazine, semicarbazide and thiosemicarbazide groups, to form an antibody-linker intermediate having substantially the same immunoreactivity and immunospecificity as the unconjugated antibody or antibody fragment; and (c) covalently attaching the linker portion of the antibody-linker intermediate to a therapeutic agent to form an antibody-therapeutic agent conjugate.

In certain circumstances, it may be desirable to separate the above-described method for preparing antibody-therapeutic agent conjugates into two parts. The first part would produce an antibody-linker intermediate which may be considered a step in the production of the final antibody-therapeutic agent conjugate. Such antibody-linker intermediates may be stored for later combination with the particular therapeutic agent. Thus, the first part of the two part method would involve steps (a) and (b) above to form the intermediate antibody-linker intermediate. The second part, possibly at a later point in time, would involve covalently attaching the linker portion of the antibody-linker intermediate to a therapeutic agent to produce the final antibody-therapeutic agent conjugate.

Such antibody-therapeutic agent conjugates can also be made by alternate methods, as, for example, by first covalently attaching the linker to the therapeutic agent, and then reacting the antibody or antibody fragment with an amine group of the linker portion of the linker-therapeutic agent to form the antibody-therapeutic agent conjugate. Thus, the invention further includes a method for preparing an antibody-therapeutic agent conjugate, comprising:

(a) reacting an antibody or antibody fragment with an oxidizing agent to form an aldehyde group in the carbohydrate moiety of the antibody or antibody fragment; and (b) reacting the aldehyde group of the resultant oxidized antibody or antibody fragment with an amine group of the linker portion of a linker-therapeutic agent intermediate, said linker-therapeutic agent intermediate, comprising a linker containing an amine group selected from the group consisting of primary amine, secondary amine, hydrazine, hydrazide, hydroxylamine, phenylhydrazine, semicarbazide and thiosemicarbazide groups, and covalently attached to a therapeutic agent, to form an antibody-therapeutic agent conjugate having substantially the same immunoreactivity and immunospecificity as the unconjugated antibody or antibody fragment.

In either of the above embodiments, the linker may comprise a spacer element and a cleavable element. One function of the spacer element could be to position the cleavable element away from the core of the antibody molecule such that the cleavable element is more accessible to the enzyme responsible for cleavage. These embodiments would involve a method for preparing an antibody-therapeutic agent conjugate comprising:

(a) reacting an antibody or antibody fragment with an oxidizing agent to form an aldehyde group in the carbohydrate moiety of the antibody or antibody fragment;

(b) reacting the aldehyde group of the resultant oxidized antibody or antibody fragment with an amine group of a linker, said linker comprising a spacer element covalently attached to a cleavable element and said amine group located on said spacer element containing an amine group selected from the group consisting of primary amine, secondary amine, hydrazine, hydrazide, hydroxylamine, phenylhydrazine, semicarbazide and thiosemicarbazide groups, to form an antibody-linker intermediate having substantially the same immunoreactivity and immunospecificity as the unconjugated antibody or antibody fragment; and (c) covalently attaching the cleavable element of the antibody-linker intermediate to a therapeutic agent to form an antibody-therapeutic agent conjugate.

Alternately, the above-described method for preparing antibody-therapeutic agent conjugates may be separated into two distinct parts. The first part (steps (a) and (b) above) would produce an antibody-linker intermediate which may be stored for later combination with a therapeutic agent (step (c) above).

These antibody-therapeutic agent conjugates in which the linker comprises a spacer element and a cleavable element may also be made by first covalently attaching the linker to the therepeutic agent, and then reacting the antibody or antibody fragment with the linker portion of the linker-therapeutic agent to form the antibody-therapeutic agent conjugate. Thus, this method for preparing an antibody-therapeutic agent conjugate (having a linker comprising a spacer element and a cleavable element) comprises:

(a) reacting an antibody or antibody fragment with an oxidizing agent to form an aldehyde group in the carbohydrate moiety of the antibody or antibody fragment; and (b) reacting the aldehyde group of the resultant oxidized antibody or antibody fragment with an amine group of a linker-therapeutic agent intermediate, said linker-therapeutic agent intermediate, comprising a spacer element covalently attached to a cleavable element and said amine group located on said spacer element and selected from the group consisting of primary amine, secondary amine, hydrazine, hydrazide, hydroxylamine, phenylhydrazine, semicarbazide and thiosemicarbazide groups, to form an antibody-therapeutic agent conjugate having substantially the same immunoreactivity and immunospecificity as the unconjugated antibody or antibody fragment.

Such antibody-therapeutic agent conjugates in which the linker comprises a spacer element and a cleavable element may be made by still other methods, for instance by first attaching the antibody to the spacer element, and then attaching the spacer element of that intermediate to a cleavable element of another intermediate comprising a cleavable element covalently attached to a therapeutic agent. Such methods comprise:

(a) reacting an antibody or antibody fragment with an oxidizing agent to form an aldehyde group in the carbohydrate moiety of the antibody or antibody fragment;

(b) reacting the aldehyde group of the resultant oxidized antibody or antibody fragment with a spacer element containing an amine group selected from the group consisting of primary amine, secondary amine, hydrazine, hydrazide, hydroxylamine, phenylhydrazine, semicarbazide and thiosemicarbazide groups, to form an antibody-spacer element intermediate having substantially the same immunoreactivity and immunospecificity as the unconjugated antibody or antibody fragment; and (c) covalently attaching the spacer element of the antibody-spacer element intermediate to a cleavable element of a cleavable element-therapeutic agent intermediate, to form an antibody-therapeutic agent conjugate.

Still another method for preparing these antibody-therapeutic agent conjugates involves first preparing an antibody-spacer element intermediate, attaching to the spacer element of this intermediate a cleavable element to form an antibody-spacer elementcleavable element intermediate, and finally attaching to the cleavable element of that intermediate a therapeutic agent. This method comprises:

(a) reacting an antibody or antibody conjugate with an oxidizing agent to form an aldehyde group in the carbohydrate moiety of the antibody or antibody fragment;

(b) reacting the aldehyde group of the resultant oxidized antibody or antibody fragment with a spacer element containing an amine group selected form the group consisting of primary amine, secondary amine, hydrazine, hydrazide, hydroxylamine, phenylhydrazine, semicarbazide and thiosemicarbizide groups, to form an antibody spacer element intermediate having substantially the same immunoreactivity and immunospecificity as the unconjugated antibody or antibody fragment;

(c) covalently attaching the spacer element of the antibody-spacer element intermediate to a cleavable element to form an antibody-spacer element-cleavable element intermediate; and (d) covalently attaching the cleavable element of the antibody-spacer element-cleavable element intermediate to a therapeutic agent to form an antibody-therapeutic agent conjugate.

Other permutations of the steps of the above-described methods may be developed from knowledge of one skilled in the art and the disclosure of this specification.

In certain instances, another function of the spacer element could be to add multiple functional sites for subsequent attachment of cleavable elements or therapeutic agents or cleavable element-therapeutic agent intermediates. Thus, one may attach to an aldehyde (or sulfhydryl) of the antibody molecule a "branched spacer element" having multiple functional sites. Such sites may be aldehyde or sulfhydryl groups, or any chemical site to which a cleavable element, therapeutic agent or cleavable element-therapeutic agent intermediate may be attached.

Furthermore, it can readily be seen that these same methods are applicable to instances in which the therapeutic agent is not cleavable from the antibody, that is, when there is no cleavable element in the linker. In these embodiments, the linker could be a "branched linker" having multiple functional sites for attachment directly to a therapeutic agent. Again, the functional sites may be aldehyde or sulfhydryl groups, or any chemical site to which a therapeutic agent may be attached.

In all of the above embodiments, several linkers, including branched linkers, may be attached to the same antibody molecule to form conjugates having a large number of therapeutic agents per antibody molecule.

The invention is also directed to intermediates and final products of the above-described methods. In particular, this invention encompasses antibody-linker intermediates, which comprise a linker attached via a covalent bond to a carbohydrate moiety of an oxidized antibody or antibody fragment, said antibody-linker intermediate having substantially the same immunoreactivity and immunospecificity of the original antibody or antibody fragment. In such intermediates the linkers may comprise a spacer element (attached to the carbohydrate moiety) which, in turn, is covalently attached to a cleavable element.

The invention also relates to antibody-spacer element intermediates, cleavable element-therapeutic agent intermediates and linker-therapeutic agent intermediates described in the methods above. Intermediates in which the linker is not cleavable are also encompassed by the invention.

Further, the invention encompasses antibody-therapeutic agent conjugates which comprise a therapeutic agent covalently attached (directly or via a linker) to a carbohydrate moiety of an oxidized antibody or antibody fragment, said antibody-therapeutic agent conjugate having substantially the same immunoreactivity and immunospecificity as the unconjugated antibody or antibody fragment.

Also encompassed by the invention are corresponding intermediates and antibody-therapeutic agent conjugates in which the linker or therapeutic agent is attached to a sulfur atom of a reduced antibody or Fab' fragment. This embodiment of the invention involves a method for preparing an antibody-therapeutic agent conjugate, comprising:

(a) reacting an antibody or the (Fab')$_2$ fragment of an antibody with a mild reducing agent to form a reduced antibody or Fab' fragment having a sulfhydryl group;

(b) reacting said sulfhydryl group with a reactive group of a linker, said linker containing a reactive group selected from the group consisting of haloalkyl groups, p-mercuribenzoate groups, and groups capable of Michael-type addition reactions, to form an antibody-linker intermediate having substantially the same immunoreactivity and immunospecificity as the unconjugated antibody or (Fab')$_2$ fragment; and (c) covalently attaching the linker portion of the antibody-linker intermediate to a therapeutic agent to form an antibody-therapeutic agent conjugate.

This method can be separated into two parts, the first part involving steps (a) and (b) above and the second step, separate in time, would involve producing the final conjugate as in step (c) above.

Alternatively, the same antibody-therapeutic agent conjugates can be made by another method, comprising:

(a) reacting an antibody or the (Fab')$_2$ fragment of an antibody with a mild reducing agent to form a reduced antibody or Fab' fragment having a sulfhydryl group; and (b) reacting said sulfhydryl group with a reactive group of a linker-therapeutic agent intermediate, said linker-therapeutic agent intermediate containing a reactive group selected from the group consisting of haloalkyl groups, p-mercuribenzoate groups, and groups capable of Michael-type addition reactions, and covalently attached to a therapeutic agent to form an antibody-therapeutic agent conjugate having substantially the same immunoreactivity and immunospecificity as the unconjugated antibody or (Fab')$_2$ fragment.

In either of the above embodiments, the linker may comprise a spacer element covalently attached to a cleavable element. As above, the spacer-element would enable positioning of the cleavable element away from the core of the antibody molecule so that the cleavable element is more accessible to the cleaving enzyme. These embodiments involve methods comprising:

(a) reacting an antibody or the (Fab')$_2$ fragment of an antibody with a mild reducing agent to form a reduced antibody or Fab' fragment having a sulfhydryl group;

(b) reacting said sulfhydryl group with a reactive group of a linker, said linker comprising a spacer element covalently attached to a cleavable element and said reactive group located on said spacer element and selected from the group consisting of haloalkyl groups, p-mercuribenzoate groups, and groups capable of Michael-type addition reactions, to form an antibody-linker intermediate having substantially the same immunoreactivity and immunospecificity as the unconjugated antibody or (Fab')$_2$ fragment; and (c) covalently attaching the cleavable element antibody-linker intermediate to a therapeutic agent to form an antibody-therapeutic agent conjugate.

Clearly, the above-described method may be separated into two parts, the first involving steps (a) and (b), and the second involving step (c) above.

These antibody-therapeutic agent conjugates having a linker comprising a spacer element and a cleavable element may be made by first covalently attaching the linker to the therapeutic agent, followed by reacting the reduced antibody or Fab' fragment with the linker portion of the linker-therapeutic agent to form the antibody-therapeutic agent conjugate. This method comprises:

(a) reacting an antibody or the (Fab')$_2$ fragment of an antibody with a mild reducing agent to from a reduced antibody or Fab' fragment having a sulfhydryl group; and (b) reacting the sulfhydryl group with a reactive group of a linker-therapeutic agent intermediate comprising a spacer element covalently attached to a cleavable element covalently attached to a therapeutic agent and said reactive group located on said spacer element and selected from the group consisting of haloalkyl groups, p-mercuribenzoate groups, and groups capable of Michael-type addition reactions, to form an antibody-linker intermediate having substantially the same immunoreactivity and immunospecificity as the unconjugated antibody or (Fab')$_2$ fragment; and These antibody-therapeutic agent conjugates having a spacer element and a cleavable element may be made by still other methods, such as by first attaching the antibody to the spacer elements, and then attaching the spacer element of that intermediate to a cleavable element of another intermediate comprising a cleavable element covalently attached to a therapeutic agent. These methods comprise:

(a) reacting an antibody or the (Fab')$_2$ fragment of an antibody with a mild reducing agent to from a reduced antibody or Fab' fragment having a sulfhydryl group;

(b) reacting said sulfhydryl group with a reactive group of a spacer element containing a reactive group selected from the group consisting of haloalkyl groups, p-mercuribenzoate groups, and groups capable of Michael-type addition reactions, to form an antibody-spacer element intermediate having substantially the same immunoreactivity and immunospecificity as the unconjugated antibody or (Fab')$_2$ fragment; and (c) covalently attaching the spacer element of the antibody-spacer element intermediate to a cleavable element of a cleavable element-therapeutic agent intermediate to form an antibody therapeutic agent conjugate.

Still another method for preparing these antibody-therapeutic agent conjugates involves first preparing an antibody-spacer intermediate, followed by attaching to the spacer element of this intermediate a cleavable element to form an antibody-spacer element-cleavable element intermediate, and finally attaching to the cleavable element of this intermediate a therapeutic agent. This method comprises:

(a) reacting an antibody or the (Fab')$_2$ fragment of an antibody with a mild reducing agent to form a reduced antibody or Fab' fragment having a sulfhydryl group;

(b) reacting said sulfhydryl group with a reactive group of a spacer element containing a reactive group selected from the group consisting of haloalkyl groups, p-mercuribenzoate groups, and groups capable of Michael-type addition reactions, to form an antibody-spacer element intermediate having substantially the same immunoreactivity and immunospecificity as the unconjugated antibody or (Fab')$_2$ fragment; and (c) covalently attaching the spacer element of the antibody-spacer element intermediate to a cleavable element to form an antibody-spacer element-cleavable element intermediate having substantially the same immunoreactivity and immunospecificity as the unconjugated antibody or Fab' fragment; and (d) attaching the cleavable element portion of an antibody-spacer element-cleavable element intermediate to a therapeutic agent.

Other permutations of the order of the steps of the above-described methods may be performed by one skilled in the art based upon this disclosure.

Additionally, spacer elements may have multiple functional sites for subsequent attachment of therapeutic agents, cleavable elements, or cleavable element-therapeutic agent intermediates. These functional sites may be aldehyde or sulfhydryl groups, or any chemical site to which the therapeutic agent, cleavable element or cleavable element-therapeutic agent may be attached.

Similarly, the above methods for attachment to sulfhydryl groups of antibodies are applicable to instances where non-cleavable linkers are employed, or where a "branched linker" is directly attached to a therapeutic agent.

In addition to all of these methods, the invention includes the intermediates of these methods in which the attachment is to a sulfur atom of an antibody molecule, including antibody-linker intermediates, antibody-spacer element intermediates, antibody-spacer element-cleavable element intermediates, linker-therapeutic agent intermediates, cleavable element-therapeutic agent intermediates. This includes intermediates and conjugates in which the linker is not cleavable.

The antibody-therapeutic agent conjugates comprise a therapeutic agent covalently attached (directly or through a linker) to a sulfur atom of a reduced antibody or Fab' fragment, said antibody-therapeutic agent conjugate having substantially the same immunoreactivity and immunospecificity as the unconjugated antibody or (Fab')$_2$ fragments.

Copending application of Goers et al., Ser. No. 650,754, filed on even date herewith, is directed specifically to embodiments involving attachment to a sulfhydryl group of a reduced antibody or Fab' fragment, and is incorporated herein by reference.

The antibody-therapeutic agent conjugates of the invention are ideally suited for in vivo therapy. Delivery of therapeutic agents to specific target sites involves administering to an animal or human an effective amount of an antibody-therapeutic agent conjugate, wherein said antibody-therapeutic agent conjugate is immunoreactive with and immunospecific for an antigenic determinant of said specific tissue and substantially non-immunoreactive with and non-immunospecific for nonspecific tissue and said antigenic determinant is not found in substantial amount in non-specific tissue.

This invention also encompasses the use of antibodies for delivery to specific cells, tissues, organs, or any other site in vivo, and the subsequent release or activation of the therapeutic agent at the target site. In one embodiment of the invention, release of the compound may be mediated by activated complement, a plasminogen activator, plasmin, a urokinase, trypsin, or another enzyme having proteolytic activity. In another embodiment of the invention, where release is not desired, photosensitive chemicals or enzymes that catalyze substrate modification with the production of cytotoxic by-products are attached to the antibody molecule.

In its most general concept, the invention contemplates site selective attachment of therapeutic agents to those areas of antibodies or antibody fragments which are not a part of nor directly involved with the antigenic site of the molecule. Thus, after selective attachment to one of these sites (located outside the antigen binding region), the antibody conjugate formed has substantially the same immunoreactivity and immunospecificity as the unconjugated antibody or antibody fragment.

Antibodies directed against any desired target (e.g., antigenic determinants of tumor cells, virus, fungi, bacteria or parasites) may be used as carrier molecules. Although conventional antibodies may be used as carrier molecules, monoclonal antibodies offer the advantages of increased specificity for antigen, improved efficiency of the delivery system and ease in production.

According to one method of the present invention, a therapeutic agent is attached to an antibody carrier molecule of an immunoglobulin class that is capable of complement activation. This attachment is accomplished via linkers which are susceptible to cleavage by an enzyme as enumerated above. One or more different therapeutic agents may be attached to each antibody molecule. The resulting antibody-therapeutic agent conjugate is administered to an individual. Subsequent to the binding of the antibody-therapeutic agent conjugate to antigen in vivo, the individual's serum complement is activated and the compounds will be selectively cleaved and released at the target site.

For release of a therapeutic agent by an enzyme other than those of the complement system, the same linker described supra may be attached to an antibody carrier molecule of a class that does not activate complement.

According to another method of the present invention, a photosensitizer is attached to an antibody carrier molecule either by a non-cleavable linker or by direct attachment to the antibody molecule. After delivery of the antibody conjugate to the target site, the photosensitizer is activiated by light of the appropriate wavelength and its cytolytic effects on nearby cells are mediated through the generation of singlet oxygen molecules and oxygen free radicals.

In an alternate embodiment of the present invention, cleavage of the linker at the target site may not be desirable. The linker utilized may be insensitive to serum proteins or the antibody molecule may be of a class or type that does not activate complement.

For the delivery of certain compounds, e.g., hormones or neurotransmitters, it may be desirable to cleave the compound without activation of the complement cascade. One may use a urokinase, tissue plasminogen activator, plasmin, trypsin or a protease-sensitive linker attached to an antibody that does or does not fix complement.

For the practice of this invention it is desirable to attach the therapeutic agent to the antibody molecule without interfering with either the antigen binding capacity of the antibody, with the ability to activate complement (also called complement fixation), or with enzyme cleavage or photoactivation of the therapeutic agent or with the process of conversion of enzyme substrates into cytotoxic by-products by the therapeutic agent. The present invention describes the novel linkers and methods of attachment which may be used to attach therapeutic agents to any antibody capable of activating complement.

4. BRIEF DESCRIPTION OF THE FIGURES

The present invention may be more fully understood by reference to the following detailed description of the invention, examples of specific embodiments of the invention and the appended figures in which:

FIG. 1 is a schematic representation of an antibody molecule or immunoglobulin of the IgG class (a), and of the IgM class (b).

FIG. 2 represents a portion of the complement cascade activated by the classical pathway. C1 through C9 represent complement proteins. The bar over certain numbers indicates an active enzyme. S' represents a site on the cell membrane.

FIG. 3 depicts a general reaction scheme for the attachment of the antineoplastic drug, Alkeran (Burroughs-Wellcome), to the peptide CBZ-gly-gly-arg.

FIG. 4 represents Sips plots of fluorescent quenching data using unmodified antibody (●—●); antibody modified by the method of the invention (Δ—Δ); and antibody modified by attachment (carbodiimide) to aspartic and/or glutamic amino acids (□—□).

FIG. 5 represents the excitation spectra for (a) unoxidized antibody and (b) antibody oxidized in accordance with Section 7.1.

FIG. 6 represents the excitation and emission spectra of the Phenylhydrazide-Tripeptide-AMC compound prepared in accordance with Section 7.2.

FIG. 7 represents the excitation and emission spectra of the Antibody-Phenylhydrazide-Tripeptide-AMC (APTA) conjugate prepared in accordance with Section 7.3.

FIG. 8 represents the results of experiments showing the specific complement mediated release of AMC along with certain controls. Fluorescence was monitored at 460 nm with excitation at 380 nm. An increase in fluorescence indicates release of AMC from the Antibody-Phenylhydrazine-Tripeptide-AMC (APTA) conjugate; (a) represents APTA conjugate incubated with glutaraldehyde-fixed sheep red blood cells and human complement; (b) represents APTA conjugate incubated with glutaraldehyde-fixed rat red blood cells and human complement; (c) represents APTA conjugate incubated with glutaraldehyde-fixed sheep red blood cells; (d) represents APTA conjugate alone.

5. DETAILED DESCRIPTION OF THE INVENTION

The present invention concerns antibody-therapeutic agent conjugates prepared by attaching a therapeutic agent to an antibody or antibody fragment directed against a target antigen. The therapeutic agent is attached either directly or via a linker to the antibody or antibody fragment. Such therapeutic agents or linkers are selectively attached to those areas of antibodies or antibody fragments which are not a part of nor directly involved with the antigen binding site of the molecule.

5.1 ANTIBODIES

According to the present invention, antibodies directed against any antigen or hapten may be used. Although conventional antibodies may be used, monoclonal antibodies offer several advantages. Each monoclonal antibody is specific for one antigenic determinant. Additionally, large amounts of each monoclonal antibody can be produced.

Antibodies used in the present invention may be directed against any determinant, e.g., tumor, bacterial, fungal, viral, parasitic, mycoplasmal, histocompatibility, differentiation and other cell membrane antigens, pathogen surface antigens, toxins, enzymes, allergens, drugs and any biologically active molecules.

For a more complete list of antigens, see U.S. Pat. No. 4,193,983, particularly columns 7-11, which patent specification is incorporated herein by reference.

Additionally, a combination of antibodies reactive to different antigenic determinants may be used.

When delivery and release of the compound attached to the antibody are desired, immunoglobulin classes that are known to activate complement are used. (See FIG. 1). In other applications, carrier immunoglobulins may be used which are not capable of complement activation. Such immunoglobulin carriers may include: certain classes of antibodies such IgM, IgA, IgD, IgE; certain subclasses of IgG; or certain fragments of immunoglobulins, e.g., half antibody molecules (a single heavy: light chain pair), or Fab, Fab' or (Fab')$_2$ fragments.

Use of antibody fragments may be advantageous for delivery of therapeutic agents because these antibody fragments permeate target sites at an increased rate. The Fab' fragments of IgG immunoglobulins are obtained by cleaving the antibody molecule with pepsin [resulting in a bivalent fragment, (Fab')$_2$] or with papain [resulting in 2 univalent fragments, (2 Fab)]. Parham, 1983, J. Immunol. 131: 2895-2902; Lamoyi and Nisonoff, 1983, J. Immunol. Meth. 56: 235-243. The bivalent (Fab')$_2$ fragment can be split by mild reduction of one or a few disulfide bonds to yield univalent Fab' fragments. The Fab and (Fab')$_2$ fragments are smaller than a whole antibody molecule and, therefore, permeate the target site or tissue more easily. This may offer an advantage for in vivo delivery since conjugates will more readily penetrate in vivo sites (e.g., tumor masses, infection sites, etc.). An additional advantage is obtained when using conjugates formed with antibody fragments because these fragments do not cross a placental barrier. As a result, using this embodiment of the present invention, a therapeutic agent may be delivered at an in vivo site (such as a tumor) to a pregnant female without exposing the fetus to the compound.

5.2. METHODS FOR ATTACHING THERAPEUTIC AGENTS TO ANTIBODIES AND ANTIBODY FRAGMENTS

The present invention utilizes several methods for attaching therapeutic agents to antibody molecules: (a) attachment to the carbohydrate moieties of the antibody or antibody fragment, or (b) attachment to sulfhydryl groups of the antibody or antibody fragment. Whichever method is used, the attachment must not significantly change the essential characteristics of the antibody or antibody fragment, such as immunospecificity and immunoreactivity. Additional considerations include simplicity of reaction and stability of the antibody conjugate produced.

5.2.1. ATTACHMENT TO OXIDIZED CARBOHYDRATE MOIETIES

Glycoproteins are biologically important macromolecules which share structural characteristics including carbohydrate residues covalently attached to a polypeptide backbone. Since antibodies are glycoproteins, compounds may be attached to the carbohydrate moiety of the molecule. Some of the carbohydrate moieties are located on the Fc region of the immunoglobulin and are required in order for C1 binding to occur. The carbohydrate moiety of the Fc region of an immunoglobulin may be utilized in the scheme described herein. Alternatively, the Fab or Fab' fragments of any immunoglobulins which contain carbohydrate moieties may be utilized in the reaction scheme described herein. An example of such an immunoglobulin is the human IgM sequenced by Putnam et al. (1973, Science 182: 287).

As explained in detail below, the carbohydrate side chains of antibodies or Fab or Fab' fragments may be selectively oxidized to generate aldehydes. The resulting aldehydes may then be reacted with amine groups (e.g., ammonia derivatives such as primary amine, secondary amine, hydroxylamine, hydrazine, hydrazide, phenylhydrazine, semicarbazide or thiosemicarbazide) to form a Schiff base or reduced Schiff base (e.g., imine, enamine, oxime, hydrazone, phenylhydrazone, semicarbazone, thiosemicarbazone or reduced forms thereof).

Alternatively, the carbohydrate moiety of the antibody may be modified by enzymatic techniques so as to enable attachment to or reaction with other chemical groups. One example of such an enzyme is galactose oxidase which oxidizes galactose in the presence of oxygen to form an aldehyde.

5.2.1.1. CHEMICAL METHODS OF OXIDATION

Oxidation of the carbohydrate portion or moiety of antibody molecules leads to formation of aldehyde groups. A variety of oxidizing agents can be used, such as periodic acid, paraperiodic acid, sodium metaperiodate and potassium metaperiodate. Among these, oxygen acids and salts thereof are preferred since secondary or undesirable side reactions are less frequent. For a general discussion, see Jackson, 1944, In Organic Reactions 2, p. 341; Bunton, 1965, Oxidation in Organic Chemistry, Vol. 1 (Wiberg, ed.), Academic Press, New York, p. 367.

Oxidation of antibodies with these oxidizing agents can be carried out by known methods. In the oxidation, the antibody is used generally in the form of an aqueous solution, the concentration being generally less than 100 mg/ml, preferably 1 to 20 mg/ml. When an oxygen acid or a salt thereof is used as the oxidizing agent, it is used generally in the form of an aqueous solution, and the concentration is generally 0.001 to 10 mM and preferably 1.0 to 10 mM. The amount of the oxygen acid or salt thereof depends on the kind of antibody, but generally it is used in excess, for example, twice to ten times as much as the amount of the oxidizable carbohydrate. The optimal amount, however, can be determined by routine experimentation.

In the process for oxidizing antibodies with oxygen acids or salts thereof, the optional ranges include a pH of from about 4 to 8, a temperature of from 0° to 37° C., and a reaction period of from about 15 minutes to 12 hours.

During the oxidation of the glycoprotein with an oxygen acid or a salt thereof, light is preferably excluded to prevent over oxidation of the glycoprotein.

5.2.1.2. ENZYMATIC METHODS OF OXIDATION

Oxidation of the carbohydrate portion of antibody molecules may also be done with the enzyme, galactose oxidase (Cooper et al., 1959, J. Biol. Chem. 234:445-448). The antibody is used in aqueous solution, the concentration being generally 0.5 to 20 mg/ml. The enzyme generally is used at about 5 to 100 units per ml of solution, at a pH ranging from about 5.5 to about 8.0.

The influence of pH, substrate concentration, buffers and buffer concentrations on enzyme reaction are reported in Cooper et al., supra.

5.2.1.3. PREPARATION OF ANTIBODY-THERAPEUTIC AGENT CONJUGATES

The antibody conjugates (or antibody linker-intermediates) of the invention may be produced by reacting the oxidized antibody with any linker or therapeutic agent having an available amine group selected from the group consisting of primary amine, secondary amine, hydrazine, hydrazide, hydroxylamine, phenylhydrazine, semicarbazide and thiosemicarbazide groups. The immediately resulting products contain a carbon-nitrogen double bond resulting from elimination of a molecule of water from the initial addition products:

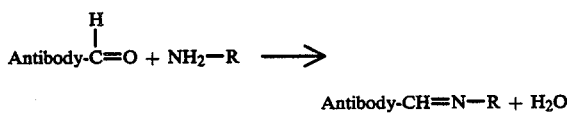

For a general discussion of the reaction of aldehydes with hydrazides, see March, 1978, In Advanced Organic Chemistry: Reactions Mechanisms and Structure, McGraw-Hill Co., New York, pp. 824–825.

A solution of the oxidized antibody at a concentration of from about 0.5 to 20 mg/ml is mixed with the therapeutic agent or linker (molar ratios of reactive amine group to antibody aldehyde ranging from about 1 to about 10,000) and the solution incubated for from about 1 to 18 hours. Suitable temperatures are from 0° to 37° C. and pH may be from about 6 to 8.

5.2.1.4. STABILIZATION OF THE ANTIBODY CONJUGATES

After the antibody-therapeutic agent conjugates (or antibody-linker intermediates) have been formed between the antibody and therapeutic agent or linker as described in Section 5.2.1.3, they can optionally be stabilized with a suitable reducing agent, such as sodium cyanoborohydride or sodium borohydride:

Reducing agent is generally added to a molar excess of from about 10 to 100 fold molar excess over available aldehyde groups. For a general discussion, see Jentoft and Dearborn, 1979, J. Biol. Chem. 254:4359.

5.2.2. ATTACHMENT TO SULFHYDRYL GROUPS

Free sulfhydryl groups can be generated from the disulfide bonds of the immunoglubulin molecule. This is accomplished by mild reduction of the antibody molecule. The disulfide bonds of IgG which are generally most susceptible to reduction are those that link the two heavy chains. The disulfide bonds located near the antigen binding region of the antibody molecule remain relatively unaffected. Such reduction results in the loss of ability to fix complement but does not interfere with antibody-antigen binding ability (Karush et al, 1979, Biochem. 18: 2226–2232). The free sulfhydryl groups generated in the intra-heavy chain region can then react with reactive groups of a linker or therapeutic agent to form a covalent bond which does not interfere with the antigen binding site of the immunoglobulin. Such reactive groups include, but are not limited to, reactive haloalkyl groups (including, for example, haloacetyl groups), p-mercuribenzoate groups and groups capable of Michael-type addition reactions (including, for example, maleimides and groups of the type described in Mitra and Lawton, 1979, J. Amer. Chem. Soc. 101: 3097–3110). By the term "haloalkyl" is meant any alkyl group of one to three carbon atoms substituted with bromine, iodine or chlorine.

Details of the conditions, methods and materials suitable for mild reduction of antibodies and antibody fragments as described generally herein may be found in Stanworth and Turner, 1973, In Handbook of Experimental Immunology, Vol. 1, Second Edition, Weir (ed.), Chapter 10, Blackwell Scientific Publications, London, which chapter is incorporated herein by reference.

Antibody-therapeutic agent conjugates (or antibody-linker intermediates) which are produced by attachment to free sulfhydryl groups of reduced immunoglobulin or reduced antibody fragments do not activate complement. Thus, these conjugates may be used in in vivo systems where cleavage and release of the therapeutic agent is not desirable (e.g., where the therapeutic agent is a photosensitizer, or an enzyme that acts on a specific substrate). Such conjugates may also be used when non-complement mediated release is desired. In such an embodiment, the therapeutic agent may be linked to sulfhydryl groups on the reduced immunoglobulin or reduced antibody fragments via linkers which are susceptible to cleavage by enzymes having proteolytic activity, including but not limited to trypsin, urokinase, plasmin, tissue plasminiogen activator and the like.

Although attachment of a therapeutic agent to sulfhydryl groups of the antibody molecule destroys the complement fixation ability of the conjugate, such methods of attachment may be used to make antibody conjugates for use in the complement-mediated release system. In such an embodiment, a therapeutic agent joined to a complement-sensitive substrate linker can be attached to sulfhydryls of reduced IgG molecules or antibody fragments and delivered to the target in a mixture with intact antibody molecules that are capable of activating complement. The latter would activate complement which would cleave the therapeutic agent from the former. The use of antibody fragments as carrier molecules in the complement mediated release system would permit the treatment of pregnant females, and offers the advantage of more rapid penetration of the conjugate into target sites.

According to one embodiment of the present invention, for attachment to sulfhydryl groups of reduced antibody molecules, the substrate linkers or the therapeutic agents are modified by attaching an iodoalkyl group to one end of the linker. The unmodified site on the linker may or may not be covalently attached to a therapeutic agent. For instance, the substrate linkers which are ester or amide linked to therapeutic agents as prepared in Section 5.5 (see Table II and Table III) are modified by the addition of an iodoalkyl group thus forming an iodoalkyl derivative as depicted below (N.B., the symbol * signifies an amide or ester bond):

As mentioned previously, the linker may be one that is susceptible or resistant to cleavage by activated complement, trypsin, plasmin, tissue plasminogen activator, urokinase or another specific enzyme having proteolytic activity.

When the iodoalkyl derivatives of the linker group are reacted with reduced antibody molecules or reduced antibody fragments, the linker group becomes covalently attached to the antibody molecules or fragment. This is depicted below (N.B. the symbol * signifies as amide or ester bond):

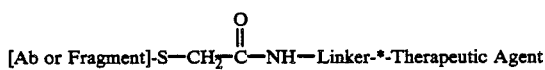

5.3. THERAPEUTIC AGENTS

Antibodies may be attached to any therapeutic agent which retains its essential properties after reaction with the antibody, and which enables the antibody to substantially retain immunospecificity and immunoreactivity. As used herein, the term "therapeutic agent" includes chemical modifications and derivatives of therapeutic agents which substantially retain their biological activity. The major limiting factor is that any attachment reaction must be selective enough to limit competing, undesirable reactions and sufficiently mild so as not to severely interfere with antibody reactivity and selectivity.

When it is desired to attach an aldehyde of the oxidized carbohydrate portion of an antibody or antibody fragment to a therapeutic agent, the therapeutic agent should contain an amine group selected from the group consisting of primary amine, secondary amine, hydrazine, hydrazide, hydroxylamine, phenylhydrazine, semicarbazide and thiosemicarbazide groups. If the therapeutic agent does not contain any such amino group, the agent can be modified to introduce a suitable amine group available for coupling.

The therapeutic agent to be attached to an antibody for use in a delivery system is selected according to the purpose of the intended application (i.e, killing, prevention of cell proliferation, hormone therapy or gene therapy). Such therapeutic agents may include, for example, pharmaceutical agents, toxins, fragments of toxins, alkylating agents, enzymes, antibiotics, antimetabolites, antiproliferative agents, hormones, neurotransmitters, DNA, radioopaque dyes, radioactive isotopes, fluorogenic compounds, marker compounds, lectins, compounds which alter cell membrane permeability, and photochemical compounds. Table I lists some of the pharmaceutical agents that may be employed in the herein described invention and in no way is meant to be an exhaustive list. Finally, combinations of therapeutic agents may be used.

TABLE I

EXAMPLES OF THERAPEUTIC AGENTS FOR ANTIBODY-MEDIATED DELIVERY

| NAME/CLASS | LINKAGE | MANUFACTURERS(S) |
|---|---|---|
| I. ANTIBACTERIALS | | |
| Aminoglycosides | | |

TABLE I-continued

EXAMPLES OF THERAPEUTIC AGENTS FOR ANTIBODY-MEDIATED DELIVERY

| NAME/CLASS | LINKAGE | MANUFACTURERS(S) |
|---|---|---|
| Streptomycin | ester/amide | |
| Neomycin | ester/amide | Dow, Lilly, Dome, Pfipharmics |
| Kanamycin | ester/amide | Bristol |
| Amikacin | ester | Bristol |
| Gentamicin | ester/amide | Upjohn, Wyeth, Schering |
| Tobramycin | ester/amide | Lilly |
| Streptomycin B | ester/amide | Squibb |
| Spectinomycin | ester | Upjohn |
| Ampicillin | amide | Squibb, Parke-Davis, Comer, Wyeth, Upjohn, Bristol, SKF |
| Sulfanilamide | amide | Merrell-National |
| Polymyxin | amide | Burroughs-Wellcome, Dow, Parke-Davis |
| Chloramphenicol | ester | Parke-Davis |
| II. ANTIVIRALS | | |
| Acyclovir | | Burroughs-Wellcome |
| Vira A | ester/amide | Parke-Davis |
| Symmetrel | amide | Endo |
| III. ANTIFUNGALS | | |
| Nystatin | ester | Squibb, Primo, Lederle, Pfizer, Holland-Rantor |
| IV. ANTINEOPLASTICS | | |
| Adriamycin | ester/amide | Adria |
| Cerubidine | ester/amide | Ives |
| Bleomycin | ester/amide | Bristol |
| Alkeran | amide | Burroughs-Wellcome |
| Velban | ester | Lilly |
| Oncovin | ester | Lilly |
| Fluorouracil | ester | Adria, Roche, Herbert |
| Methotrexate | amide | Lederle |
| Thiotepa | — | Lederle |
| Bisantrene | — | Lederle |
| Novantrone | ester | Lederle |
| Thioguanine | amide | Burroughs-Wellcome |
| Procarabizine | — | Hoffman La Roche |
| Cytarabine | — | Upjohn |
| V. RADIOPHARMACEUTICALS | | |
| $^{125}I$ | | |
| $^{131}I$ | | |
| $^{99m}Tc$ (Technetium) | | |
| VI. HEAVY METALS | | |
| Barium | | |
| Gold | | |
| Platinum | | |
| VII. ANTIMYCOPLASMALS | | |
| Tylosine | | |
| Spectinomycin | | |

According to one embodiment of the present invention, photochemicals including photosensitizers and photothermolytic agents may be used as therapeutic agents. Efficient photosensitizers include, but are not limited to porphyrins and modified porphyrins (e.g., hematoporphyrin, hematoporphyrin dihyddrazide, deuteroporphyrin dihydrazide and protoporphyrin dihydrazide), rose bengal, acridines, thiazines, xanthenes, anthraquinones, azines, flavin and nonmetal-containing porphyrins, porphyrin-like compounds, methylene blue, eosin, psoralin and the like. Other photosensitizers include, but are not limited to tetracyclines (e.g., dimethylchlor tetracycline) sulfonamides (e.g., sulfanilamide), griseofulvin, phenothiazines, (e.g., chlorpromazine), thiazides, sulfonylurea, and many others. Photochemicals may be designed or synthetically prepared to absorb light at specific wavelengths. Photothermolytic agents, such as Azure A, which are activated at the site of action by a light source (see Anderson and Parrish, 1983, Science 220: 524–527) may be utilized as therapeutic agents.

According to another embodiment of the present invention, enzymes that catalyze substrate modification with the production of cytotoxic by-products may be used as therapeutic agents. Examples of such enzymes include but are not limited to glucose oxidase, galactose oxidase, xanthene oxidase and the like.

5.4. LINKERS

According to the invention, antibodies may be covalently attached to a therapeutic agent through an intermediate linker having at least two reactive groups, one to react with antibody and one to react with the therapeutic agent. The linker, which may include any compatible organic compound, must be chosen such that the reaction with antibody (or therapeutic agent) does not adversely affect antibody reactivity and selectivity. Furthermore, the attachment of linker to therapeutic agent must not destroy the activity of the therapeutic agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present invention, suitable linkers for attachment to reduced antibodies or antibody fragments include those having certain reactive groups capable of reaction with a sulfhydryl group of a reduced antibody or Fab' fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097–3110). By the term "haloalkyl" is meant any alkyl group of one to three carbon atoms substituted with bromine, iodine or chlorine.

The therapeutic agent may be attached to the linker before or after the linker is attached to the antibody molecule. In certain applications it may be desirable to first produce an antibody-linker intermediate in which the linker is free of an associated therapeutic agent. Depending upon the particular application, a specific therapeutic agent may then be covalently attached to the linker.

5.4.1. BRANCHED LINKERS

Of additional interest are "branched linkers" which have multiple sites for attachment of therapeutic agents. For multiple site linkers, a single covalent attachment to an antibody or antibody fragment would result in an antibody-linker intermediate capable of binding a therapeutic agent at a number of sites. The sites may be aldehyde or sulfhydryl groups or any chemical site to which therapeutic agents can be attached.

Alternatively, higher specific activity (or higher ratio of therapeutic agents to antibody molecule) can be achieved by attachment of a single site linker at a plurality of sites on the antibody or antibody fragment. This plurality of sites may be introduced into the antibody or antibody fragment by either of two methods. First, one may generate multiple aldehyde groups and/or sulfhydryl groups in the same antibody molecule. Second, one may attach to an aldehyde or sulfhydryl of the antibody molecule a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the antibody or antibody fragment.

5.4.2. CLEAVABLE LINKERS

Peptide linkers which are susceptible to cleavage by enzymes of the complement system, urokinase, tissue plasminogen activator, trypsin, plasmin, or another enzyme having proteolytic activity may be used in one embodiment of the present invention. According to one method of the present invention, a therapeutic agent is attached via a linker susceptible to cleavage by complement. The antibody is selected from a class which can activate complement. The antibody-therapeutic agent conjugate, thus, activates the complement cascade and releases the therapeutic agent at the target site. According to another method of the present invention, a therapeutic agent is attached via a linker susceptible to cleavage by enzymes having a proteolytic activity such as a urokinase, a tissue plasimogen activator, plasmin, or trypsin.

In addition therapeutic agents may be attached via disulfide bonds (for example, the disulfide bonds on a cystine molecule) to the antibody molecule. Since many tumors naturally release high levels of glutathione (a reducing agent) this can reduce the disulfide bonds with subsequent release of the therapeutic agent at the site of delivery.

5.4.3. SPACERS AND CLEAVABLE ELEMENTS

In still another embodiment, it may be necessary to construct the linker in such a way as to optimize the spacing between the therapeutic agent and the antibody. This may be accomplished by use of a linker of the general structure:

$$W-(CH_2)_n-Q$$

wherein
  W is either $-NH-CH_2-$ or $-CH_2-$;
  Q is an amino acid, peptide; and
  n is an integer from 0 to 20.

In still other embodiments, the linker may comprise a spacer element and a cleavable element. The spacer element serves to position the cleavable element away from the core of the antibody molecule such that the cleavable element is more accessible to the enzyme responsible for cleavage. Certain of the "branched linkers" described above may serve as spacer elements.

Throughout this discussion, it should be understood that the attachment of linker to therapeutic agent (or of spacer element to cleavable element, or cleavable element to therapeutic agent) need not be particular mode of attachment or reaction. Any reaction providing a product of suitable stability and biological compatibility is acceptable.

5.4.4. SERUM COMPLEMENT AND SELECTION OF LINKERS

According to one method of the present invention, when release of a therapeutic agent is desired, an antibody of a class which can activate complement is used.

The resulting conjugate retains the ability to bind antigen and activate the complement cascade.

Complement is the collective name for a group of serum proteins which can be activated in one of two ways, the classical pathway and the properdin pathway (Müller-Eberhard, Hospital Practice, August 1977:33-43). The classical pathway is initiated by the binding of antibodies of the IgM class or certain subclasses of IgG to its corresponding antigen whereas the properdin pathway is dependent upon the serum protein, properdin and other non-immunoglobulin serum factors (Reid and Porter, 1981, Ann. Rev. Biochem. 50:433-464).

The classical pathway is a pathway of particular importance of the practice of the present invention. The classical pathway is characterized by the formation of certain antibody-antigen complexes (or immune complexes) which activate the proteolytic enzymes of the complement system (Borsos and Rapp, 1965, J. Immunol. 95:559-566; Cohen, 1968, J. Immunol. 100:407-413; Cohen and Becker, 1968, J. Immunol. 100:403-406; Ishizaka et al., 1968, J. Immunol. 100:1145-1153). These activated complement enzymes cleave and activate other components of the complement cascade (FIG. 2). Ultimately the formation of an "attack complex" (or lytic complex) is induced resulting in disruption of target cell membrane integrity.

The first component activated in the classical pathway is C1 which becomes a protease that acts on both C2 and C4. Activated C1 ($\overline{C1}$) has a specific esterase activity. Activated C4,2 ($\overline{C4,2}$), sometimes called C3 convertase, is a complex which proteolytically cleaves C3, and together with activated C3 (C3b), cleaves C5. Cleavage of C3 is the first step in common between the classical and properdin pathways of complement activation.

The enzymatic activities of both $\overline{C1}$ and $\overline{C4,2}$ have been studied in vitro with synthetic peptide substrates (see Table II) which are cleaved at a carboxy terminal ester or amide bond. These synthetic peptide substrates may be used as linkers between an antibody molecule and a therapeutic agent as described in the present invention, or as cleavable elements of linkers having a spacer element and a cleavable element. Such linkers may allow for the specific complement mediated cleavage and subsequent release of the therapeutic agent in its active form at the target site. However, any substrate which is susceptible to cleavage by any of the components of complement, trypsin, tissue plasminogen activator, urokinase, plasmin, or any enzyme having proteolytic activity may be used as a linker.

Thus, according to this embodiment of the present invention, a therapeutic agent is joined to one end of the cleavable linker or cleavable element and the other end of the linker group is attached to a specific site on the antibody molecule. For example, if the therapeutic agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the therapeutic agent contains functional groups that would interfere with attachment to the linker, these interfering functional groups can be blocked before attachment and deblocked once the product conjugate or intermediate is made. For example, FIG. 3 depicts a general reaction scheme for the attachment of the antineoplastic drug, Alkeran (Burroughs-Wellcome) to the peptide CBZ-gly-gly-arg. The opposite or amino terminus of the linker is then used either directly or after further modification for binding to an antibody molecule which is capable of activating complement.

Linkers (or spacer elements of linkers) may be of any desired length, one end of which can be covalently attached to specific sites on the antibody molecule. The other end of the linker or spacer element may be attached to an amino acid or peptide linker. Table III lists some cleavable elements that may be used as linker groups to prepare the antibody-therapeutic agent conjugates of the present invention. (In the table n may be an integer including zero.) These sequences were derived from those of the complement substrate sequences by substituting amino acids with similar acid-base properties. This list is not exhaustive.

Thus when these conjugates bind to antigen in the presence of complement the amide or ester bond which attaches the therapeutic agent to the linker will be cleaved, resulting in release of the agent in its active form. These conjugates, when administered to an individual, will accomplish delivery and release of the therapeutic agent at the target site, and are particularly effective for the in vivo delivery of pharmaceutical agents, antibiotics, antimetabolites, antiproliferative agents and the like.

TABLE II

| SYNTHETIC SUBSTRATES FOR COMPLEMENT COMPONENTS | Reference No.* |
|---|---|
| For $\overline{C1}$: | |
| N—Boc-tyrosine o-nitrophenyl ester | 1 |
| N—Boc-phenylalanine o-nitrophenyl ester | 1 |
| N—Boc-lysine o-nitrophenyl ester | 1 |
| N—CBZ—tyrosine p-nitrophenyl ester | 2 |
| For $\overline{C4,2}$: | |
| N—acetyl-gly-lys-methyl ester | 3 |
| N—CBZ—lys-methyl ester | 3 |
| N—acetyl-lys-methyl ester | 3 |
| Boc-leu-gly-arg-7-amino-4-methylcoumarin | 4 |

*1. Sim et al., 1977, Biochem. J. 163:219-27.
2. Bing 1969, Biochemistry 8: 4503-10.
3. Cooper N. R., 1975, Biochemistry 14:4245-51.
4. Caparale et al., 1981, J. Immunol. 128:1963-65.

TABLE III

LINKER GROUPS FOR ATTACHMENT OF THERAPEUTIC AGENTS (TA) TO ANTIBODY MOLECULES[1]

A.        Linkers For Cleavage by $\overline{C1}$

-lys-
H$_2$N—(a.a.)$_n$-    -tyr-       -*-TA
                 -phe-
                 -arg- B.        Tripeptide Sequences For Cleavage by $\overline{C4,2}$ -leu-ala-arg-
                 -leu-ala-lys-
                 -leu-ala-tyr-
                 -leu-leu-arg-
                 -leu-leu-lys-
                 -leu-leu-tyr-
                 -leu-gly-arg-
H$_2$N—(a.a.)$_n$-    -leu-gly-lys-       -*-TA
                 -leu-gly-tyr-
                 -leu-val-arg-
                 -leu-val-lys-
                 -leu-val-tyr-
                 -leu-ile-arg-

TABLE III-continued
LINKER GROUPS FOR ATTACHMENT OF THERAPEUTIC AGENTS (TA) TO ANTIBODY MOLECULES[1]

| | | |
|---|---|---|
| | -leu-ile-lys- | |
| | -leu-ile-tyr- | |
| | -ala-ala-arg- | |
| | -ala-ala-lys- | |
| | -ala-ala-tyr- | |
| | -ala-leu-arg- | |
| | -ala-leu-lys- | |
| | -ala-leu-tyr- | |
| | -ala-gly-arg- | |
| $H_2N$—(a.a.)$_n$- | -ala-gly-lys- | -\*-TA |
| | -ala-gly-tyr- | |
| | -ala-val-arg- | |
| | -ala-val-lys- | |
| | -ala-val-tyr- | |
| | -ala-ile-arg- | |
| | -ala-ile-lys- | |
| | -ala-ile-tyr- | |
| | -gly-ala-arg- | |
| | -gly-ala-lys- | |
| | -gly-ala-tyr- | |
| | -gly-leu-arg- | |
| | -gly-leu-lys- | |
| | -gly-gly-arg- | |
| $H_2N$—(a.a.)$_n$- | -gly-gly-lys- | -\*-TA |
| | -gly-gly-tyr- | |
| | -gly-val-arg- | |
| | -gly-val-lys- | |
| | -gly-val-tyr- | |
| | -gly-ile-arg- | |
| | -gly-ile-lys- | |
| | -gly-ile-tyr- | |
| | -val-ala-arg- | |
| | -val-ala-lys- | |
| | -val-ala-tyr- | |
| | -val-leu-arg- | |
| | -val-leu-lys- | |
| | -val-leu-tyr- | |
| | -val-gly-arg- | |
| $H_2N$—(a.a.)$_n$- | -van-gly-lys- | -\*-TA |
| | -val-gly-tyr- | |
| | -val-val-arg- | |
| | -val-val-lys- | |
| | -val-val-tyr- | |
| | -val-ile-arg- | |
| | -val-ile-lys- | |
| | -val-ile-tyr- | |
| | -ile-ala-arg- | |
| | -ile-ala-lys- | |
| | -ile-ala-tyr- | |
| | -ile-leu-arg- | |
| | -ile-leu-lys- | |
| | -ile-leu-tyr- | |
| | -ile-gly-arg- | |
| $H_2N$(a.a.)$_n$- | -ile-gly-lys- | -\*-TA |
| | -ile-gly-tyr- | |
| | -ile-val-arg- | |
| | -ile-val-lys- | |
| | -ile-val-tyr- | |
| | -ile-ile-arg- | |
| | -ile-ile-lys- | |
| | -ile-ile-tyr- | |
| C. | Peptide Sequences for Cleavage by $\overline{C4,2}$ | |
| | -leu-gly- | |
| | -leu-leu- | |
| | -leu-ala- | |
| | -leu-val- | |
| | -leu-ile- | |
| | -gly-gly- | |
| | -gly-leu- | |
| | -gly-ala- | |
| | -gly-val- | |
| $H_2N$— | -ala-gly- | -Tripeptide[2]-\*-TA |
| | -ala-leu- | |
| | -ala-ala- | |
| | -ala-val- | |
| | -ala-ile- | |
| | -val-gly- | |
| | -val-leu- | |
| | -val-ala- | |
| | -val-val- | |
| | -val-ile- | |
| | -ile-gly- | |
| | -ile-leu- | |
| | -ile-ala- | |
| | -ile-val- | |
| | -ile-ile- | |

[1]The asterisk (\*) represents either an amide bond (Linker-C—NH—TA)
       ‖
       O or an ester bond (Linker-C—O—TA).
       ‖
       O

[2]Tripeptide represents any of the tripeptides listed in Table III B.

5.4.5. LINKERS FOR RELEASE WITHOUT COMPLEMENT ACTIVATION

In yet another application of targeted delivery, release of the therapeutic agent without complement activation is desired since activation of the complement cascade will ultimately lyse the target cell. Hence, this approach is useful when delivery and release of the therapeutic agent should be accomplished without killing the target cell. Such is the goal when delivery of cell mediators such as hormones, enzymes, corticosteroids, neurotransmitters, genes or enzymes to target cells is desired. These conjugates may be prepared by attaching the therapeutic agent to an antibody molecule or fragment that is not capable of activating complement via a linker that is mildly susceptible to cleavage by serum proteases. When this conjugate is administered to an individual, antigen-antibody complexes will form quickly whereas cleavage of the therapeutic agent will occur slowly, thus resulting in release of the compound at the target site.

In accordance with this embodiment of the invention, the substrate linkers are modified, for example, by attaching hydrazine or hydrazide derivatives to one end of the linker. The unmodified sites on the linker may or may not be covalently attached to a therapeutic agent. For instance, the substrate linkers which are attached to a therapeutic agent via an ester or amide link, as described in Section 5.5 (see Table II and Table III) are modified by attaching a hydrazide (e.g., phenylhydrazine) to the opposite amino terminus of the peptide chain. This results in the following structure (N.B., the symbol \* signifies an amide or ester bond):

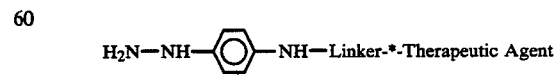

H$_2$N—NH—⬡—NH—Linker-\*-Therapeutic Agent

Although in the structure shown the hydrazine is in the para position, one may alternatively use compounds with the hydrazine moiety in the ortho or meta positions. These hydrazide derivatives of the peptide linkers which are attached to a therapeutic agent via an ester or amide bond are then reacted with an oxidized immunoglobulin, or immunoglobulin fragment containing an oxidized carbohydrate. This results in hydrazone formation and the covalent attachment of the therapeutic agent to the carbohydrate side chain of the immunobe resistant to cleavage by either activated complement or serum proteases.

In embodiments in which the linker is designed to be susceptible to cleavage by a serum protease, one resulting structure is schematically represented below (N.B., the symbol * signifies an amide or ester bond):

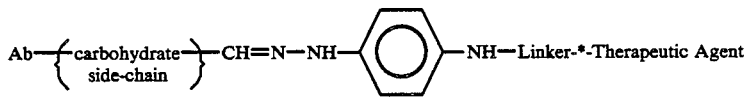

5.4.6. NON-CLEAVABLE LINKERS OR DIRECT ATTACHMENT

In still other embodiments of the invention, the conjugate may be designed so that the therapeutic agent is delivered to the target but not released. This may be accomplished by attaching a therapeutic agent to an antibody or antibody fragment either directly or via a non-cleavable linker.

5.4.6.1. NON-CLEAVABLE LINKERS

These non-cleavable linkers may include amino acids, peptides, D-amino acids or other organic compounds which may be modified to include functional groups that can subsequently be utilized in attachment to antibody molecules or antibody fragments by the methods described herein. A general formula for such an organic linker could be

wherein
- W is either —NH—CH$_2$— or —CH$_2$—;
- Q is an amino acid, peptide; and
- n is an integer from 0 to 20.

5.4.6.2. NON-CLEAVABLE CONJUGATES

Alternatively, a compound may be attached to antibody molecules or antibody fragments which do not activate complement. When using carrier antibodies that are incapable of complement activation, this attachment may be accomplished using linkers that are susceptible to cleavage by activated complement or using linkers that are not susceptible to cleavage by activated complement.

5.5. USES OF ANTIBODY-THERAPEUTIC AGENT CONJUGATES

The antibody-therapeutic agent conjugates of the invention are useful in a variety of therapeutic in vivo applications. Throughout this application the term "cellular disorder" is meant to include all neoplasms, including cancers, adenomas, and hyperplasias; certain immunological disorders, including autoimmune diseases, graft-versus-host diseases (e.g., after bone marrow transplantation), immune suppressive diseases, e.g., after kidney or bone marrow transplantation. Treatment of such cellular disorders involving, for example, bone marrow transplantation, may include purging (by killing) undesired cells, e.g., malignant cells or mature T lymphocytes.

Therapeutic applications center generally on treatment of various cellular disorders, including those broadly described above, by administering an effective amount of the antibody-therapeutic agent conjugates of the invention. The properties of the antibody are such that it is immunospecific for and immunoreactive with a particular antigen render it ideally suited for delivery of therapeutic agents to specific cells, tissues, organs or any other site having that particular antigen.

According to this aspect of the invention, the antibody or antibody fragment of the antibody therapeutic agent conjugate functions to deliver the conjugate to the target site.

The choice of antibodies, linkers, and compounds used to make the conjugates depends upon the purpose of delivery. The delivery and release or activation of therapeutic agents at specific target sites may result in selective killing or inhibition of proliferation of tumor cells, cancer cells, fungi, bacteria, parasites, or virus. The targeted delivery of hormones, enzymes, or neurotransmitters to selected sites may also be accomplished. Ultimately the method of the present invention may have an application in gene therapy programs wherein DNA or specific genes may be delivered in vivo or in vitro to target cells that are deficient in that particular gene. Additionally, the conjugates may be used to "turn off" or prevent the activation of oncogenes, such as myc, ras and the like.

In vivo administration may involve use of therapeutic agents of antibody therapeutic agent conjugates in any suitable adjuvant including serum or physiological saline, with or without another protein, such as human serum albumin. Dosage of the conjugates may readily be determined by one of ordinary skill, and may differ depending upon the nature of the cellular disorder and the therapeutic agent used. Route of administration may be parenteral, with intravenous administration generally preferred.

5.5.1. PHOTORADIATION THERAPY

One type of photoradiation therapy (also referred to in this context as photoimmunotherapy) which advantageously uses the antibody-therapeutic agent conjugates of this invention encompasses the treatment of disorders by combining the phototoxic effects of certain compounds and the site specific attachment of the antibody to a target site. The photosensitizer is activated by a light source and its cytotoxic effect is mediated through the production of singlet oxygen which results in toxicity to neighboring cells. This effect involves the participation of molecular oxygen. (For a more complete overview of this topic see Parrish, 1981, J. Investig. Derm. 77:45–50).

The specificity of the photochemical reaction can be maintained by selecting the proper wavelength and specific photosensitizer (or chromophore) to be used depending on the biologic effect desired. It may be possible to attach more than one photosensitizer for delivery to a target site. Depending upon the wave length and effect desired therapeutic agents might be activated i a synergistic fashion. The photosensitizer may e activated at the target site with lasers or other light sources via optical fibers or any other appropriate method.

5.5.2. SUBSTRATE MODIFICATION

In an alternate embodiment of the present invention, substrate activation by the therapeutic agent may be used to mediate formation of singlet oxygen or peroxides and induce cell killing. In this particular embodiment, the therapeutic agent is an enzyme. For example, galactose oxidase will oxidize galactose and some galactose derivatives at the $C_6$ position. In the course of the oxidation reaction, molecular oxygen is converted into hydrogen peroxide which is toxic to neighboring cells. The enzyme glucose oxidase, a flavoenzyme, may also be used in the embodiment of this invention. This enzyme is highly specific for $\beta$-D-glucose and can act as an antibiotic due to peroxide formation. The enzyme may be attached to an antibody molecule either directly or via a non-cleavable linker. An individual is given an effective dosage of this conjugate and is then perfused with substrate. Cell killing is mediated through the formation of peroxides by the methods described above. The toxic effect of peroxides may be amplified by administration of a second enzyme, preferably of human origin, to convert its peroxide to a more toxic hypochlorous acid. Examples of suitable enzymes include but are not limited to myeloperoxidase, lactoperoxidase and chloroperoxidase.

5.5 ADVANTAGES OF ANTIBODY-THERAPEUTIC AGENT CONJUGATES

According to one embodiment of the present invention, a therapeutic agent may be attached to an antibody directed against a target antigen. The chemical linking methods described herein allow the resulting antibody conjugate to retain the ability to bind antigen and to activate the complement cascade (when the unconjugated antibody or antibody fragment had such ability). As a result, when the conjugate is administered to an individual, the subsequent formation of immune complexes with target antigens in vivo activates the individual's serum complement linker is designed to be susceptible to cleavage by complement, the compound will be cleaved at the target site by one or more of the enzymes of the complement cascade. Since release of the compound occurs after delivery to the target site the efficiency of the target delivery system is greatly improved.

The method of the present invention offers another advantage over other targeting systems. For example, it is known that all cells of a tumor do not each possess the target antigenic determinant. Thus, delivery systems which require internalization into the target cell will effect successful delivery only to those tumor cells that possess the antigenic determinant and that are capable of internalizing the conjugate. Tumor cells that do possess the antigenic determinant or are incapable of this internalization, will escape treatment.

According to the method of the present invention, antibody carrier molecules deliver the therapeutic agent to the target cells. More importantly, however, once attached to the target cell, the method described in the present invention allows the release or activation of the active or activatable therapeutic compound. Release or activation may be mediated by the individual's activated complement enzymes, tissue plasminogen activator, urokinase, plasmin or another enzyme having proteolytic activity, or by activation of a photosensitizer or substrate modification. Once released, the therapeutic agent is then free to permeate the target sites, e.g., tumor mass. As a result, the therapeutic agent will act on tumor cells that do not possess the antigenic determinant. Additionally, the entire process is not dependant upon internalization of the conjugate.

The following examples will serve to further typify the nature of the invention without being a limitation on the scope thereof.

6. EXAMPLES: SERIES I

The purpose of this series of examples is to demonstrate that the methods for preparing antibody conjugates described in the present invention do not adversely affect the antigen binding properties of antibodies in the way the carbodimide reaction affects such properties. To this end, the carbohydrate moieties of a mouse monoclonal IgM, specific for the phosphorylcholine group, were oxidized and covalently attached to the 1,6-diaminohexyl derivative of ethylene diamine di-(o-hydroxyphenylacetic acid) [EDDHA]to form 1,6-diaminohexyl-EDDHA. For comparative purposes, 1,6-diaminohexyl-EDDHA as well as unmodified EDDHA were attached to identical samples of IgM monoclonal antibody using the carbodiimide reaction. Under these conditions, the 1,6-diaminohexyl-EDDHA would couple to available aspartic and glutamic acid residues, while the unmodified EDDHA would couple to available lysines.

The binding properties of these samples were compared with the native antibody in order to evaluate affinity and homogeneity.

6.1. OXIDATION OF MOUSE MONOCLONAL IgM

A mouse monoclonal IgM antibody specific for the ligand, phosphorylcholine, was oxidized at a concentration of 2 mg/ml in phosphate buffered saline (PBS, 0.01 M phosphate, 0.15 M sodium chloride), pH 6.0. The antibody-containing solution was cooled in a water-ice bath, and 56.8 ug of sodium metaperiodate was added (40 ul of a 1.42 mg/ml solution; final periodate concentration=0.26 mM). This reaction mixture was incubated for one hour, after which 2 ul of ethylene glycol was added. This was incubated an additional thirty minutes. The sample was then passed through a Sephadex ® G-25 column equilibrated with PBS and the protein fractions pooled.

ATTACHMENT OF LINKER TO EDDHA

EDDHA (1.5 g, 4.2 mmole) and triethylamine (1.2 ml, 8.4 mmole) were mixed with 40 ml of water. This heterogeneous solution was heated to 60° C. and stirred vigorously for 0.5 hour. The solution was dried in vacuo and then was dissolved in 400 ml of dry N,N-dimethylformamide. The solution was then cooled in an ice bath and iobutylchloroformate (0.56 ml, 4.2 mmole) was added. The reaction mixture was stirred with cooling for 0.5 hours. The resulting triethylamine hydrochloride precipitate was removed by filtration and the filtrate containing the mixed carboxycarbonic anhydride of EDDHA was red in color.

1-amino-6-trifluoroacetamidohexane (0.8 g, 4.1 mmole) was added to the above carboxycarbonic anhydride of EDDHA. The homogeneous solution was stirred at 4° C. for 0.5 hour, then was lyophilized to yield an oily product. The oil was washed with an acetone/ether (4:1) mixture to yield a crude yellow product. The solid 1-amino-6-trifluoroacetamidohexyl-EDDHA was collected and hydrolyzed with 7%

K$_2$CO$_3$ and reprecipitated with HCl at pH 4 to yield pure 1,6-diaminohexyl-EDDHA (1.4 g). This compound gives a positive ninhydrin test and thin layer chromatography shows only one spot. In the presence of basic solution of an equal molar quantity of TbCl$_3$, excitation at 295 nm yielded emission at 545 nm, due to formation of the characteristic energy transfer chelate complex between EDDHA and terbium ion.

6.3. PREPARATION OF IgM-LINKER-EDDHA CONJUGATES

The antibody, oxidized by the method of Section 6.1, was incubated with an approximately 270-fold molar excess of 1,6-diaminohexyl-EDDHA, prepared by the method of Section 6.2, for one hour at room temperature. This was followed by addition of solid sodium cyanoborohydride to a final concentration of 10 mM, and further incubation of 4 hours at room temperature. The mixture was then dialyzed at 4° C. versus several changes of PBS, and concentrated by ultrafiltration.

6.4. CARBODIIMIDE ATTACHMENT OF LINKER-EDDHA TO IgM

To 263 ul IgM antibody (1.9 mg/ml) was added 10 mg of 1-ethyl-3-(3-dimethylaminopropyl) carbodiimide (1 ml of 10 mg/ml solution, pH 5.0) and PBS (pH 5.0) to make up to 2.5 ml. The mixture was incubated two hours at room temperature. Ten ul of 1M ethanolamine was then added and incubated for one hour at room temperature. This was then dialyzed overnight against PBS (pH 7.0).

6.5. CARBODIIMIDE ATTACHMENT OF EDDHA TO IgM

To 263 ul IgM antibody (1.9 mg/ml) was added 10 mg of 1-ethyl-3-(3-dimethylaminopropyl) carbodiimide (1 ml of 10 mg/ml solution, pH 5.0) and PBS (pH 5.0) to make up to 2.5 ml. The mixture was incubated for two hours at room temperature. To this was added 2.75 ml of 0.01M EDDHA (pH 5.5) and the solution was incubated for two hours at room temperature. Ten ul 1M of ethanolamine was added and the mixture incubated for one hour at room temperature. This was then dialyzed overnight against PBS (pH 7.0).

6.6. EFFECTS OF CARBOHYDRATE-MEDIATED ATTACHMENT TO ANTIBODIES

The affinities of unmodified mouse monoclonal antibody and antibody conjugates prepared according to Sections 6.3, 6.4 and 6.5, all specific for the phosphorycholine group, were measured by fluorescence quenching according to the methods described by Rodwell and Karush, 1983, J. Immunol. 130:313-316, incorporated herein by reference.

The Sips plots presenting data for antibody carbodiimide conjugates and antibody conjugates of the invention are shown in FIG. 4. The binding measurements clearly demonstrate the retention of specificity, affinity, and homogeneity for the sample modified via the carbohydrate attachment methods of the invention, (Δ—Δ), when compared to the unmodified antibody (●—●).

The association constant for the binding of the phosphorylcholine derivative was measured to be $8.1 \times 10^5 M^{-1}$ for the unmodified antibody and $1.1 \times 10^6 M^{-1}$ for the carbohydrate-attached antibody conjugate.

In contrast to this, the antibody preparation of Section 6.4, modified by a carbodiimide reaction (□—□) has substantially reduced binding, probably below the calculated value of $2.4 \times 10^5 M^{-1}$. The antibody preparation of Section 6.5, also modified by a carbodiimide reaction, showed even further reduced binding. The association constant for this antibody preparation was at least an order of magnitude below that measured for the unmodified antibody (too low to be accurately determined by this technique).

The assumption of a heterogeneity index of unity in the Sips analysis is valid for the data reduction only if the sample is homogeneous (monoclonal). A check on the actual homogeneity (monoclonal nature) of the sample is the correlation coefficient or fit of the experimental data points with the calculated line in the Sips plot. Inspection of the plots of FIG. 4 clearly shows good agreement for the unmodified antibody and carbohydrate-attached antibody and very poor agreement for those with carbodiimide-attachments. This is most likely due to the lack of selectivity of the carbodiimide attachment method. Lysines, glutamic and aspartic acids occur in all parts of antibody molecules, including the antigen binding regions. As a result, at least some of the antibodies are modified at or near the binding sites with consequent effects on interaction with antigen. The sites of attachment to carbohydrate, however, are specific and distal from the binding site, and provide little, if any, change in binding properties as shown in these experiments.

7. EXAMPLES: SERIES II

The following examples illustrate methods for the specific attachment of an antibody molecule to a compound of interest via a linker.

While the compound attached in these experiments is not considered a therapeutic agent, its use illustrates specific covalent attachment to the oxidized carbohydrate moiety of an antibody via a linker. By analogous mechanisms, a therapeutic agent may be attached to prepare an antibody-therapeutic agent conjugate.

7.1. OXIDATION OF THE CARBOHYDRATE MOIETY OF THE ANTIBODY MOLECULE

The antibody molecule used in this example was a monoclonal IgM (designated no. 171) specific for antigenic determinants on sheep red blood cells. To prepare the monoclonal antibody, Lewis rats were immunized with a single injection of sheep red blood cells. Three days later, spleen cells from the immunized rats were harvested and fused with the myeloma line SP2/0 Ag14 according to the method of McKearn et al., 1979, Immunol. Rev. 47:91-115. Cloned cells were then grown and the resulting monoclonal antibody was purified as described by Kliman and McKearn, 1981, J. Immunol. Meth. 42: 1-9.

Oxidation of the antibody carbohydrate moiety was accomplished by reacting the antibody with galactose oxidase by a modification of the method of Cooper et al., supra. To this end, 3.8 mg of no. 171 monoclonal antibody was added to 1 ml of buffer consisting of 0.135 M NaCl, 0.015 Tris-HCl (pH 7.0), 0.5 mM MgCl$_2$, and 0.15 mM CaCl$_2$. Subsequently, a 0.1 ml aliquot of a solution of galactose oxidase (Worthington Biochemical Co., Freehold, N.J.) at a concentration of 52 units of enzyme/ml of the same buffer was added to the antibody solution. Finally, 43 ug of catalase (Worthington Biochemical Co., Freehold, NJ) dissolved in an additional 0.1 ml of the same buffer was added to the reaction mixture (the catalase was added to degrade hydrogen peroxide that is generated during the oxidation reaction). The reaction mixture was incubated for 48 hours at room temperature, then stored at 4° C. FIG. 5 represents the excitation spectra for unoxidized (a) and oxidized (b) antibodies.

7.2. PREPARATION OF THE TRIPEPTIDE-AMC FOR ATTACHMENT TO THE ANTIBODY MOLECULE

For the purposes of the present example, a synthetic fluorogenic compound was utilized as the conjugate partner. The properties of this synthetic compound are such that the bound and free states of the fluorogenic compound are spectrofluorometrically distinguishable. The synthetic fluorogenic compound used was obtained from Serva Fine Biochemicals, Inc., Garden City Park, LI, N.Y. (Catalog #51474). This compound consists of a tripeptide (Gly-Gly-Arg) attached via an amide linkage to the fluorescent compound 7-amino-4-methyl coumarin (AMC); the amino group of glycine is blocked by carbobenzoxy chloride (Cbz). The structure of this compound (hereinafter Tripeptide-AMC or Gly-Gly-Arg-AMC) is shown below:

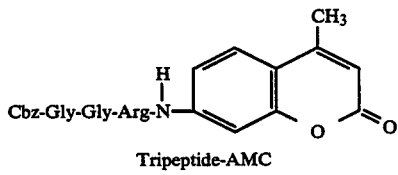

Tripeptide-AMC

The excitation and emission maxima of free AMC (345 nm and 445 nm, respectively) differ from those for AMC bound to the tripeptide (325 nm and 395 nm, respectively). This affords a means for distinguishing between the bound and free forms of the AMC molecule using a fluorometric assay. Excitation and emission wavelengths of 383 nm and 455 nm may be used for optimum differences for assay purposes; at these wavelengths, free AMC retains 20% of its maximal fluorescence but possesses a relative fluorescence 500-fold greater than an equimolar amount of bound AMC (Zimmerman et al., 1978, Proc. Natl. Acad. Sci., U.S.A. 75(2):750-753).

A hydrazine derivative of the Tripeptide-AMC compound was prepared. Aldehyde groups of the oxidized carbohydrate side chain of the antibody molecule were then reacted with the hydrazine derivative to form a hydrazone.

In order to attach a hydrazine derivative (e.g., 4-fluorophenylhydrazine), the Tripeptide-AMC was first deblocked at the glycine amino terminus by removal of the Cbz group. This was accomplished by dissolving the Tripeptide-AMC in trifluoroacetic acid (Sigma, St. Louis, MO), and bubbling HBr gas (Matheson, East Rutherford, NJ) through the solution for 45 minutes. The product, $H_2N$-Gly-Gly-Arg-NH-AMC, was precipitated by the addition of cold diethyl ether (Baker Chemical Co., Phillipsburgh, N.J.), and dissolved in absolute ethanol (Publicker Industries Co., Linfield, P.A.). An equimolar amount of 4-fluorophenylhydrazine (Aldrich Chemical Co., Milwaukee, W.I.) in absolute ethanol was added with mixing. After incubation in the dark at room temperature for 2 hours, the reaction mixture was stored in the dark at 4° C. The resulting product (Phenylhydrazine-Tri-peptide-AMC) has the structure:

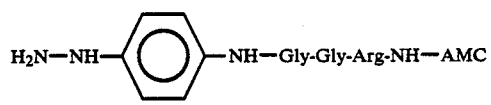

This compound was shown to be positive for fluorescence by exciting with ultraviolet light, and positive for the presence of a hydrazine group. The hydrazine linked to the tripeptide was detected by thin layer chromatography (TLC) using a spray of a 0.1% trinitrobenzene sulfonic acid aqueous solution for the colorimetric determination of a hydrazine (a pinkish or orange-brown color indicates the presence of hydrazine). The results of TLC demonstrated the presence of a hydrazine group at the migratory band of the Tripeptide-AMC.

The absorption and emission spectra for the Phenylhydrazine-Tripeptide-AMC compound as shown in FIG. 6 reveal a similarity to the Tripeptide-AMC spectra, but a shift in excitation and emission maxima consistent with the covalent modification of the Phenylhydrazine- Tripeptide-AMC. The maxima for excitation and emission of the Phenylhydrazine-Tripeptide-AMC compound are 345 nm and 385 nm, respectively. The product was precipitated from solution with cold diethyl ether, washed, and dissolved in dimethylsulfoxide (Baker Chemical Co., Phillipsburgh, N.J.).

7.3. ATTACHMENT OF PHENYLHYDRAZINETRIPEPTIDE-AMC TO THE OXIDIZED CARBOHYDRATE MOIETY OF THE ANTIBODY MOLECULE

The oxidized monoclonal antibody preparation described in Section 7.1, supra, was adjusted to pH 5.1 by the addition of a small amount of 0.1 M acetate buffer (pH 5.0). An estimated 10-fold excess of Phenyl-hydrazine-Tripeptide-AMC (prepared in Section 7.2) was added to the antibody solution, which was then incubated at 37° C. in the dark, overnight (approximately 14 hours). The reaction mixture was then chromatographed on a Sephadex ® G-25 column (Pharmacia Fine Chemicals, Piscataway, N.J.) in order to remove any unreacted Phenyl-hydrazine-Tripeptide-AMC.

Spectrofluorometric analysis of the protein fractions confirmed the presence of the Phenylhydrazine-Tripeptide-AMC covalently attached to the antibody (Antibody-Phenylhydrazine-Tripeptide-AMC). The excitation and emission maxima for the conjugate are 325 nm and 385 nm, respectively (FIG. 7). The large peak at 285 nm in the excitation spectrum of the conjugate may be explained by tryptophan absorption with residual fluorescence at 385 nm and may also be the result of resonance energy transfer from the amino acid tryptophan of the antibody molecule to AMC.

8. EXAMPLES: SERIES III

The following examples illustrate specific release of the compound from the antibody conjugate prepared by the methods of Section 7. These antibody conjugates retain the ability to fix complement as revealed by a hemolytic complement fixation assay. Furthermore, the specific release of the compound from the antibody conjugate, at the antigenic cell surface, via enzymatic cleavage by the complement system is demonstrated by a non-hemolytic assay.

In the following examples the compound is fluorogenic. Thus, the complement mediated release of the fluorescent compound may be detected by an assay capable of differentiating between the bound and free forms of the fluorescent molecule.

While the compound released in this example is not considered a therapeutic agent, its use illustrates enzymatic cleavage of a linker by the complement system or a serum enzyme having proteolytic activity. By analogous cleavage mechanisms, a therapeutic agent may be released from an antibody-therapeutic agent conjugate.

The materials and procedures of Section 7.1 were used as described to oxidize the carbohydrate moieties of monoclonal antibodies (No. 171).

In the presence of sheep red blood cells and serum complement, these monoclonal antibodies (No. 171) activate the complement enzyme cascade (a result of antigen-antibody binding). Complement fixation causes lysis of the sheep red blood cells which results in the release of hemoglobin. The released hemoglobin may be detected spectrophotometrically, thus providing an assay for complement fixation.

The Tripeptide-AMC was prepared as described in Section 7.2. The properties of the fluorogenic compound (AMC) are such that the bound and free states of the fluorogenic compound are spectrofluorometrically distinguishable. This provides a definitive assay for measuring the complement fixation ability of the antibody conjugate. More importantly, it provides a means for quantitating the subsequent complement-mediated release of the compound.

The specific covalent attachment of phenylhydrazine-tripeptide-AMC to the oxidized carbohydrate moieties of the antibodies was performed as described in Section 7.3.

8.1. COMPLEMENT FIXATION ASSAYS

Two types of complement fixation assays were utilized, hemolytic and fluorometric. These assays determined whether the Antibody-Phenylhydrazine- Tripeptide-AMC conjugate retained complement fixation ability, and whether AMC was cleaved by complement.

8.1.1. PREPARATION OF HUMAN COMPLEMENT

A 10 ml sample of freshly drawn human whole blood was clotted on ice for 17 hours. The clot was removed by centrifugation, and the resulting human serum was frozen in 0.5 ml aliquots. Human complement was shown to be active in these samples by the hemolytic assay described in Section 8.1.2.

8.1.2 HEMOLYTIC ASSAY FOR COMPLEMENT FIXATION

A 200 ul aliquot of a suspension of sheep red blood cells (Gibco Diagnostics, Madison, Wis.) at an approximate concentration of $2 \times 10^8$ cells/ml were mixed with 20 ul of the Antibody-Phenylhydrazine-Tripeptide-AMC conjugate mixture prepared in Section 7.3 (approximately 2 ug of protein). After 15 minutes of mixing and incubating at 37° C., 100 ul of the human serum complement (prepared in Section 8.1.1.) was added to the mixture. After 30 min to 1 hour of incubation at 37° C., the mixture was centrifuged to pellet the cells. The extent of the complement-mediated cell lysis was determined by spectrophotometrically measuring hemoglobin released into the supernatant (412 nm).

The results of this assay demonstrated complete hemolysis and essentially 100% binding of antibody to cell surface. For example, addition of distilled water to a pellet formed be centrifuging 200 ul of the sheep red blood cell suspension completely lyses the cells, and releases hemoglobin. A 1:20 dilution of the supernatant of sheep red blood cells which were completely lysed in distilled water had an $O.D._{412}$ of 0.646. An identical dilution of sheep red blood cells which were lysed by the addition of conjugate an complement had an $O.D._{412}$ of 0.672. Thus the conjugate retained the ability to bind antigen and to fix complement.

8.1.3. NON-HEMOLYTIC ASSAY FOR COMPLEMENT MEDIATED RELEASE OF AMC

Conditions for the non-hemolytic assay were identical to those above except that glutaraldehydefixed sheep red blood cells (Sigma, St. Louis, Mo.) were used in place of normal sheep red blood cells. Glutaraldehyde fixed cells do not lyse in the presence of antibody and complement and, therefore, no hemoglobin is released Instead, a fluorometric assay is used to demonstrate the release of the AMC. A non-hemolytic system is necessary for use in the fluorometric assay, because the presence of hemoglobin interferes with fluorescence measurements in this system. Prior to use in the assay, these fixed red blood cells were shown to bind both the unmodified antibody and the Antibody-Phenylhydrazine-Tripeptide-AMC which was prepared in Section 7.3.

The non-hemolytic assay was used to show the specific complement-mediated release of the AMC from the antibody conjugate. Similarly to the hemolytic assay, 00 ul of the glutaraldehyde-fixed sheep red blood cells, at an approximate concentration of $2 \times 10^8$ cells/ml, was incubated with the Antibody-Phenylhydrazide-Tripeptide-AMC conjugate at 37° C. for 15 minutes.

After centrifuging and resuspension in buffer, 50 ul of the human complement preparation (Section 8.1.1) was added, and the fluorescence at 460 nm monitored, with excitation at 380 nm (Caporale et al., 1981, J. Immunol. 128:1963-65.) as a function of time. As controls, the conjugate was incubated with sheep red blood cells alone; in the presence of rat red blood cells and human complement (the monoclonal antibody used does not bind to rat red blood cells); and in the absence of both sheep red blood cells and complement (the monoclonal antibody used does not bind to rat red blood cells). FIG. 8 shows the results of these experiments. A comparison of curve (a) which represents the conjugate incubated with glutaraldehyde-fixed sheep red blood cells and human complement to the control curves labeled (b), (c) and (d) clearly demonstrates the release of free AMC in the sample containing the specific antibody target and human complement. Thus, curve (b) which represents the conjugate incubated with glutaraldehyde-fixed rat red blood cells and human complement, curve (c) which represents the conjugate incubated with glutaraldehyde-fixed sheep red blood cells, and curve (d) which represents the conjugate alone demonstrate no release of AMC.

9. EXAMPLES: SERIES IV

According to one embodiment of the present invention a therapeutic agent may be attached to an antibody or antibody fragment via a linker that is susceptible to cleavage by complement or other proteolytic enzymes. Such antibody-conjugates are particularly useful for therapeutic applications where it is desired to release the therapeutic agent at the target site in the body. As detailed in Section 5, the antibody-therapeutic agent conjugates may be prepared either by attaching a therapeutic agent to an antibody-linker intermediate, or by attaching an antibody to a linker-therapeutic agent intermediate.

In the following examples (Series IV and V) either AMC or the amino acid tyrosine, covalently attached to a linker, e.g., Gly-Gly-Arg, was released via enzymatic cleavage. While the compounds (AMC and tyrosine) released by the cleavage of the linker in these examples are not considered therapeutic agents, their use illustrates enzymatic cleavage by serum enzymes such as trypsin, urokinase and plasmin and tissue plasminogen activator. By analogous mechanisms, a therapeutic agent may be cleaved by such enzymes from the linker-therapeutic agent intermediates of the present invention.

In Series IV, the AMC or tyrosine was enzymatically cleaved from a free linker. In Series V, the AMC or tyrosine was enzymatically cleaved from a free antibody-linker conjugate and from an antibodylinker conjugate bound to a target cell. Thus, comparison of results from the two series of experiments illustrates the effect of the leaving group (AMC or tyrosine) on the rate of cleavage, as well as the effect of the environment (i.e., free linker versus free antibody-linker conjugate versus antibody-linker conjugate bound to a target cell).

9.1. CLEAVAGE OF THE TRIPEPTIDE-AMC BY TRYPSIN AND UROKINASE

For the purposes of this experiment, a synthetic fluorogenic compound Gly-Gly-Arg-AMC obtained from Serva Fine Biochemicals, Inc., Garden City Park, N.Y. was utilized.

The rates of cleavage for the peptide linker were measured by fluorescence quenching using a Perkin Elmer 650-10S fluorescence spectrometer (Perkin-Elmer Corporation, Norwalk, Conn.). The excitation and emission wavelengths were 380 nm and 460 nm, respectively and the temperature was maintained at 25° C. with a Lauda k-2/R circulating water bath (Brinkmann Instruments, Westbury, N.Y.).

The initial concentrations of Gly-Gly-Arg-AMC were determined by optical density, $\Sigma^{1M}{}_{325} = 16,000$. The solutions were adjusted to 1 uM concentrations. One ml of the 1 uM solution in PBS, pH 7.4 was placed in a cuvette. The appropriate amounts of enzyme (1 ug/ml trypsin or 10 ug/ml urokinase) was then added at room temperature with stirring using a motor-driven syringe and the reaction kinetics were followed for several minutes. The fluorescence intensity of a known concentration of free AMC was established and used as a baseline to determine the change in units per nM/minute of free AMC in this fluorescence assay system. The results of the assay are described in Table IV.

TABLE IV

ENZYMATIC CLEAVAGE

| Section[1] | Substrate | Released Group Substrate Concentration | Cleavage Rates nM/min. Trypsin[2] 1 ug/ml | Urokinase 10 ug/ml |
|---|---|---|---|---|
| 9.1 | Gly—Gly—Arg—AMC | 1 uM | 35 | 16 |
| 9.1 | Gly—Gly—Arg—AMC | 1 uM | 75 | 60 |
| 9.1 | Gly—Gly—Arg—AMC | 1 uM | 170 | 78 |
| 9.1 | Dextran-Gly—Gly—Arg—AMC | 1 uM | 8.4 | .9 |
| 9.1 | Gly—Gly—Arg—AMC | 100 uM | 20,000 | not determined |
| 9.3 | Gly—Gly—Arg—Tyr* | 0.1 uM | 4 | .01 |
| 9.4 | Pro—Gly—Arg—Val—Val—Gly—Tyr* | 0.1 uM | 3 | .01 |

[1]Section = section in which experiment is described.
[2]100 ug/ml Trypsin was used in the experiment in which the Gly—Gly—Arg—AMC substrate concentration was 100 uM.

In another experiment, the Gly-Gly-Arg-AMC concentration was 100 uM and the trypsin used at 100 ug/ml. The results of this assay are also described in Table IV. In another embodiment of the present invention, the Gly-Gly-Arg-AMC was conjugated to oxidized dextran which can serve as a spacer as described in Section 5.4.3 (10,000 molecular weight) (Pharmacia Fine Chemicals, Piscataway, N.J.) by the methods of the present invention using a molar ratio of Gly-Gly-Arg-AMC to dextran of 58:1. Dextran-Gly-Gly-Arg-AMC was separated with a 6.5 ml Sephadex ® G-25 column (Pharmacia Fine Chemicals, Piscataway, N.J.).

Rates of enzymatic cleavage of the dextran-Gly-Gly-Arg-AMC, using the methods of this section, are also summarized in Table IV

9.2. CLEAVAGE OF TRIPEPTIDE-AMC DERIVATIVES BY UROKINASE, TRYPSIN, PLASMIN AND PURIFIED COMPLEMENT COMPONENTS $\overline{C4,2}$ and $\overline{C1s}$ Peptide sequences that are analogs of complement components were cleaved by trypsin (0.1 ug/ml), urokinase (0.1 ug/ml), plasmin (1 ug/ml) and purified complement components $\overline{C4,2}$ and $\overline{C1s}$ (40 ug/ml). The data in Table V compare the cleavage rates (nM/minute) of these sequences. The fluorescence assay described in Section 8 for cleavage of Gly-Gly-Arg-AMC was used here. Complement components were purified and assayed by the method of Tack and Prahl (Biochem., 1976, 15:4513–4521).

TABLE V

Cleavage of Tripeptide-AMC Derivatives by Urokinase, Trypsin, Plasmin and Purified Components $\overline{C4,2}$ and $\overline{C1s}$

| PEPTIDE (5 uM) | Urokinase (0.1 ug/ml) | Trypsin (0.1 ug/ml) | Plasmin (1 uM) | $\overline{C1s}, \overline{C4,2}$ (40 ug/ml) | $\overline{C1s}$ (10 ug/ml) |
|---|---|---|---|---|---|
| Z—Gly-Gly-Arg-AMC | 27 | 450 | 0.005 | 0.9–1.2 | 0.9–1.2 |
| Glu-Gly-Arg-AMC | 35 | 140 | — | — | — |
| Boc-Val-Gly-Arg-AMC | 2.8 | 720 | — | — | — |
| Boc-Leu-Gly-Arg-AMC | 3.7 | 750 | — | — | — |
| Boc-Val-Gly-Arg-AMC | 2.8 | 720 | — | — | — |
| Boc-Phe-Ser-Arg-AMC | 0.044 | 17 | — | — | — |
| Boc-Val-Pro-Arg-AMC | 0 | 3.8 | — | — | — |
| Boc-Glu-Arg-Arg-AMC | 0 | 3.7 | — | — | — |
| Glu-Lys-Lys-AMC | 0 | 0.62 | — | — | — |
| Pro-Phe-Arg-AMC | 0 | 0 | — | — | — |

9.3. CLEAVAGE OF GLY-GLY-ARG-TYR* BY UROKINASE AND TRYPSIN

For the purposes of the present example, the tetrapeptide Glycine-Glycine-Arginine-Tyrosine was radiolabeled at the amino acid residue tyrosine with 125 Iodine (125 I) (Greenwood et al. 1963, Biochem. J. 88: 114–120). This radiolabeled compound is hereinafter referred to as Gly-Gly-Arg-Tyr* (wherein the * denotes $^{125}$I). The properties of this radiolabeled peptide are such that the bound and free states can be readily assayed for the release of the $^{125}$I labeled tyrosine residue after cleavage with the appropriate amount of enzyme (1 ug/ml trypsin or 10 ug/ml urokinase).

The peptide Gly-Gly-Arg-Tyr* was assayed for the release of the 125I labeled tyrosine residue by agarose gel electrophoresis or thin-layer chromatography (TLC, Sono and Asakura, 1974, Biochem 13:4386–4394). Briefly, appropriate amounts of enzyme were added to a reaction tube containing 0.1 uM Gly-Gly-Arg-Tyr in PBS, pH 7.4. The mixture was incubated at 37° C. for 30 minutes. Three ul of this reaction mixture were then applied to an agarose gel (1%) and run at high voltage (120 V/cm) in Barbitol Buffer, 0.025 M sodium diethylbarbituate HCl buffer, pH 8.6. Three ul of bromophenol blue solution was used as a marker to determine the end of the run. The agarose gel was then cut into sections and counted in a LKB 1271 gamma counter (LKB Instruments, Gaithersburg, Md.) to determine if the Tyr remained at the origin or migrated through the gel. Alternatively, samples were separated and identified by TLC as described supra. Samples were spotted on TLC plates after incubation with the enzyme and run in 4:1:1 BAW solvent (butanol:acetic acid:water) until the solvent front was one inch from the top of the plate. The plate was dried and divided into ten sections which were counted in a gamma counter. The 125I labeled tyrosine residue will migrate further than the unlabeled peptide in this system.

In both systems the peptide is cleaved as described below:

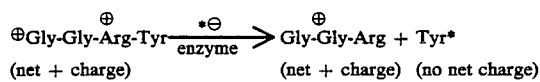

The rates of cleavage for trypsin and urokinase are summarized in Table IV.

9.4. CLEAVAGE OF A PLASMINOGEN ANALOG BY TRYPSIN AND UROKINASE

In the following experiments, an $^{125}$I radiolabled plasminogen analog Pro-Gly-Arg-Val-Val-Gly-Tyr was synthesized by standard peptide solid phase synthetic methods (Barany and Merrifield, In The Peptides, Vol. 2, E. Gross and J. Meinhofer, eds., Academic Press, N.Y., 1980, pp 1–180). It was cleaved by the enzymes trypsin (1 ug/ml) and urokinase (10 ug/ml), as described above and assayed by TLC in the BAW solvent system described supra. The peptide is cleaved as described below:

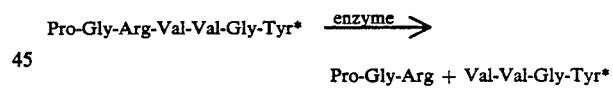

In these assays the radiolabeled Tyr* residue of the peptide migrated farther than the unlabeled portion The rates of cleavage are summarized in Table IV.

9.5. CLEAVAGE OF A PURIFIED COMPLEMENT COMPONENT ANALOG

In another experiment, an $^{125}$I radiolabeled C3 complement component analog

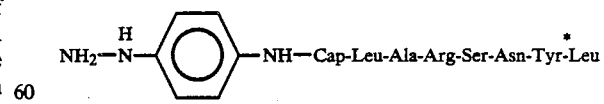

covalently attached to phenylhydrazine aminocaproic acid (NH-Cap) prepared by solid phase synthesis (Barany and Merrifield, supra) was cleaved by purified complement component C1s (10 ug/ml) and C1N, C42 (40 ug/ml). Complement components were purified by the method of Tack and Prahl, 1976, Biochem. 15:4513–4521. The peptide is cleaved as follows:

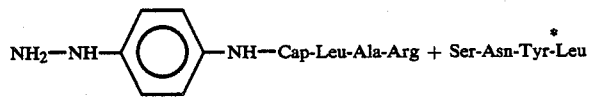

In these assays the radiolabeled Tyr residue of the peptide migrated farther than the unlabeled portion. The rates of cleavage are summarized in Table VI.

TABLE VI
ENZYMATIC CLEAVAGE

| | | Cleavage Rates nM/min. | |
|---|---|---|---|
| Substrate | Released Group Substrate Concentration | $\overline{C1s}$ 10 ug/ml | $\overline{C1s}$, $\overline{C4,2}$ 40 ug/ml |
| NH$_2$—NH—⟨◯⟩—NH—Cap-Leu-Ala-Arg-Ser-Asn-Tyr*-Leu | 5 uM | .01 | .01 |

10. EXAMPLES: SERIES V

Two specific monoclonal antibodies were utilized in the following experiments (NS 4.1-Mouse IgM against sheep red blood cells and LL 151-Mouse IgG against sheep red blood cells).

10.1. FORMATION OF ANTIBODY-GLY-GLY-ARG-TYR* CONJUGATES

Radiolabeled antibody-Gly-Gly-Arg-Tyr* conjugates were prepared according to one method of the present invention as described below. The carbohydrate moiety of the antibody (LL 1151) was oxidized by reacting approximately 1 mg/ml of antibody in phosphate buffered saline (PBS) with 110 ul of 100 mM sodium metaperiodate (NaIO$_4$) at pH 6 (to give a final concentration of 10 mM (NaIO$_4$) for 1 hour on ice in the dark.

Gly-Gly-Arg-Tyr*, prepared by the method of Section 9.2, was coupled to normal human IgG or LL 1151 or NS 4.1 antibody oxidized by the method of Section 12.1 infra, by incubating the antibody at a 300-fold molar excess of Gly-Gly-Arg-Tyr* in the 0.1 M phosphate buffer, pH 6.0. To reduce the imine, sodium cyanoborohydride (NaCNBH3) was added to a final concentration of 10 mM, and the reaction mixture was maintained at room temperature for 2 hours. Unreacted Gly-Gly-Arg-Tyr* was separated from the antibody conjugate by gel filtration. The sample was passed through a 5 ml Sephadex® G-50 column (Pharmacia Fine Chemicals, Piscataway, N.J.), which had been pre-coated with 1 ml of 10% BSA and run in PBS, pH 7.4. The protein fractions were pooled.

10.2. CLEAVAGE OF ANTIBODY-GLY-GLY-ARG-TYR* CONJUGATES BY TRYPSIN AND UROKINASE

The antibody-Gly-Gly-Arg-Tyr* conjugates prepared by the method of Section 10.1 were assayed for the release of the 125I tyrosine residue by gel filtration after cleavage of the linker. The conjugate was cleaved by the enzyme trypsin (100 ug/ml or 10 ug/ml) or urokinase (100 ug/ml) as described in Section 9.2, and the mixture was chromatographed on a Sephadex® G-50 column. In this system, the cleaved Tyr* was retarded by the column. Therefore cleavage was determined by the loss of radioactivity in the void volume peak after gel filtration on the column. The antibody-peptide was cleaved as follows:

results of this experiment are summarized in Table VII.

TABLE VII
ENZYMATIC CLEAVAGE OF ANTIBODY CONJUGATES

| | | % cleaved (based on loss of [125] Tyr) | | | |
|---|---|---|---|---|---|
| | | Trypsin | | Urokinase | |
| Section[1] | Substrate | 100 ug/ml | 10 ug/ml | 100 ug/ml | 10 ug/ml |
| 10.2 | NS 4.1-Gly—Gly—Arg—Try* | 33 | 27 | 3 | |
| 10.2 | LL 1151-Gly—Gly—Arg—Tyr* | 33 | 18 | 1 | |
| 10.3 | GSRBC-NS 4.1-Gly—Gly—Arg—Tyr* | | | 28 | 6 |
| 10.3 | GSRBC-LL 1151-Gly—Gly— | | | | |

TABLE VII-continued
ENZYMATIC CLEAVAGE OF ANTIBODY CONJUGATES

| | | % cleaved (based on loss of $^{125}$ Tyr) | | |
| | | Trypsin | | Urokinase | |
| Section[1] | Substrate | 100 ug/ml | 10 ug/ml | 100 ug/ml | 10 ug/ml |
|---|---|---|---|---|---|
| | Arg—Tyr* | | 19 | | — |

[1]Section = section in which experiment is described.

10.3. ATTACHMENT OF THE ANTIBODY-GLY-GLY CONJUGATES TO CELLS AND ENZYMATIC CLEAVAGE

This experiment illustrates cleavage of Tyr* from antibody-Gly-Gly-Arg-Tyr* conjugates, wherein the antibody conjugate was attached to an antigenic determinant of a cell.

Twenty ml of glutaraldehyde-fixed sheep red blood cells (GSRBC, 1×10⁹ cells/ml) were washed in Buffer I (0.15 M NaCl, 0.05 M Tris, 0.1 mg/ml BSA, pH 8.0) and resuspended in 2 ml of Buffer I. The cells were incubated with LS 1151-Gly-Gly-Arg-Tyr* (or NS 4.1 Gly-Gly-Arg-Tyr*) prepared by the method of Section 10.1 for 30 minutes at 0° C., then for 30 minutes at 37° C., washed several times with Buffer I and finally resuspended in 10 ml Buffer I. Either of the enzymes trypsin (10 ug/ml) or urokinase (10 ug/ml) was added to 1 ml aliquots of cells and incubated for 0, 15, 60, and 180 minutes at 37° C. Controls were treated in a similar manner but without the addition of enzyme. After incubation at 37° C. the cells were washed with buffer, resuspended in 1 N NaOH, and counted in a LKB 1271 gamma counter (LKB Instruments, Gaithersburg, Md.). The percent of loss of counts per minute (CPM) compared to the control was calculated to be the amount of Tyr* cleaved.

The results are summarized in Table VII.

10.4 FORMATION AND CLEAVAGE OF CELL-ANTIBODY GLY-GLY-ARG-AMC

This experiment illustrates the cleavage of AMC from an antibody-Gly-Gly-Arg-AMC conjugate attached to a target cell.

Two ml of glutaraldehyde fixed sheep red blood cells (GSRBC, 1×10⁹ cells/ml) were washed in EDTA (ethylenediaminetetraaceticacid) - VBS gel buffer. The pellet was incubated with an LL 1151 Gly-Gly-Arg-AMC conjugate, prepared using the same methods described in Section 12.1 infra and incubated for 30 minutes at 37° C., and then for 30 minutes at 0° C. This mixture was washed with EDTA-VBS gel buffer and resuspended in 2.2 ml PBS, pH 7.4. The mixture was separated into two portions. Trypsin (1 ug/ml) or urokinase (1 ug/ml) was then added to one portion of the resuspended material. The other portion was the control. The conjugate was then incubated at 37° C. At various times during the incubation period, the mixture was centrifuged and the fluorescence of the supernatant was measured using a Perkin Elmer 650-10S fluorescence spectrophotometer as described in Section 6.2. The fluorescence of a known concentration of bound AMC (control) was determined and the change in nM/minute after cleavage was calculated. The results are summarized in Table VIII.

TABLE VIII
CLEAVAGE OF AMC FROM ANTIBODY CONJUGATE ATTACHED TO TARGET CELL

| | Cleaveage Rate (nM/min.) | |
| Substrate | Trypsin | 1 ug/ml Enzyme Urokinase |
|---|---|---|
| GSRBC-LL 1151-Gly—Gly—Arg—AMC | 0.48 | 0.14 |

11. EXAMPLES: PREPARATION OF PORPHYRIN DERIVATIVES

The following examples illustrate the novel derivatives of porphyrin which can be used as photoactivatible cytolytic agents (or photosensitizers) for in vivo therapy when specifically attached to an antibody molecule.

11.1. PREPARATION OF DEUTEROPORPHYRIN DIHYDRAZIDE

Commercially available deuteroporphyrin dimethyl ester (98%, 0.05 g, 0.093 mmole), obtained from Aldrich Chemicals, Milwaukee, Wis., was suspended in 10 ml dry methanol and 10 ul anhydrous hydrazine (9.0 mg, 0.28 mmole) was added. The solution was refluxed for approximately 4 hours and then evaporated to produce a deep red solid.

11.2. PREPARATION OF PROTOPORPHYRIN DIHYDRAZIDE

Commercially available protoporphyrin dimethyl ester (345 mg, 6.0 mmole) obtained from Aldrich Chemicals, Milwaukee, Wis., was suspended in 30 ml dry methanol. Anhydrous hydrazine (48.0 mg, 1.5 mmole, 47.4 ul) was added and the solution refluxed for 24 hours. Evaporation gave a deep red solid which was only slightly soluble in many organic solvents.

11.3. PREPARATION OF HEMATOPORPHYRIN DIMETHYL ESTER

Commercially available hematoporphyrin 3.0 g, 5 mmole) was obtained from Aldrich Chemicals, Milwaukee, Wis., suspended in 50 ml dry methanol in a 250 ml erlenmeyer flask equipped with a magnetic stirrer and cooled to 0° C. in an ice bath. A solution of ethereal diazomethane approximately 17 mmoles in about 125 ml ether) was added slowly over a period of 25 minutes with constant stirring. The mixture was stirred at 0° C. for one hour and then at room temperature overnight in the dark. Evaporation of the solution produced a deep red solid which was separated by the technique of thin-layer chromatography (Sono and Asakura, 1974, Biochem. J. 13:4356-4394) using a developing solvent composed of 5% methanol and 95% chloroform. Several components were identified, including a major component which gave a large pink spot with an $R_f$ value of 0.14. The dimethyl ester could be converted to the corresponding dihydrazide by standard treatment with methanolic hydrazine.

11.4. PREPARATION OF HEMATOPORPHYRIN DIHYDRAZIDE

Hematoporphyrin free base (0.5 g, $8.35 \times 10^{-4}$ mole, Sigma Chemical Co., St. Louis, Mo.) was dissolved in 200 ml of dry N,N-dimethylformamide and 0.24 ml of triethylamine was added and stirred under nitrogen gas for 20 minutes at room temperature. This homogeneous solution was cooled in an ice bath and 0.218 ml isobutylchloroformate ($1.67 \times 10^{-3}$ mole) was added. After stirring for one-half hour, 0.132 ml ($4.16 \times 10^{-3}$ mole) anhydrous hydrazine was added. The solution was stirred in the dark at 4° C. for one hour and for one hour at room temperature.

The solution was dried with a Rotary Evaporator (Rotavap, Buchi, Brinkmann Instruments, Westbury, N.Y.) to give a deep red residue. Distilled water was added to the residue and the solution was adjusted to pH 12 with 1N NaOH to yield more of the precipitate. The solid product was removed by filtration, washed with distilled water and dried in a vacuum dryer to give a deep red crystals.

12. EXAMPLE: ATTACHMENT OF HEMATOPORPHYRIN DIHYDRAZIDE TO ANTIBODY

The specific mouse monoclonal antibody utilized in the following experiments was CYT-021. The antibody is a monoclonal IgG which is specific for a glycoprotein antigen on human cytotoxic/suppressor T-lymphocytes.

12.1 PREPARATION OF ANTIBODY-HEMATOPORPHYRIN DIHYDRAZIDE CONJUGATES

The hematoporphyrin dihydrazide was attached to the CYT-021 antibody for use in photoradiation treatment of cellular disorders. Antibody-hematoporphyrin dihydrazide conjugates were prepared according to one method of the instant invention by first oxidizing the carbohydrate moiety of the antibody molecule. The carbohydrate moiety of CYT-021 antibody was oxidized by reacting approximately 1 mg/ml of antibody in phosphate buffered saline (PBS) with 110 ul of 100 mM sodium metaperiodate (NaIO4) at pH 6 (to give a final concentration of 10 mM NaIO4) for 1 hour on ice in the dark.

Excess NaIO4 was removed by passing the solution through a 10 ml Sephadex ® G-50 column (Pharmacia Fine Chemicals, Piscataway, N.J.) which had been pre-washed with 1 ml of a 10% bovine serum albumin (BSA) solution in phosphate buffered saline (PBS). The protein was eluted with PBS, pH 6 and 1 ml fractions were collected, OD280 determined and the protein fractions were pooled. The oxidized CYT-021 antibody was then attached to hematoporphyrin dihydrazide as described below and the CYT-021 antibody-hematoporphyrin dihydrazide conjugate either used immediately or stored frozen at −20° C. protected from light.

Hematoporphyrin dihydrazide was coupled to oxidized CYT-021 antibody as follows. A solution of hematoporphyrin dihyrazide was prepared by dissolving 5 mg of hematoporphyrin dihydrazide in 50 ul of N,N-dimethylformamide (DMF). The concentration of hematoporphyrin dihydrazide was adjusted to 1 mg/ml by the addition of 5 ml of deionized water.

500 ul of oxidized CYT-021 antibody, in PBS, pH 6.0 was incubated with an equal volume of the hematoporphyrin dihydrazide solution for 30 minutes in the dark, at room temperature. To reduce the hydrazone product, sodium cyanoborohydride (NaCNBH3) was added to a final concentration of 10 mM and the reaction mixture was incubated overnight at room temperature.

Free hematoporphyrin dihydrazide, in PBS, pH 6.0, was removed by passing the reaction mixture over a ml Sephadex ® G-50 column (Pharmacia Fine Chemicals, Piscataway, N.J.) which had been pre-washed with 1 ml of a solution of BSA in PBS. The protein was eluted with PBS, pH 6 and 1 ml fractions were collected, and protein fractions were pooled. The amount of hematoporphyrin dihydrazide bound to CYT-021 antibody was determined spectrophotometrically by using the extinction coefficients for protein at 280 nm and hematoporphyrin dihydrazide at 374 nm, and ranged from 4 to 8 moles/mole antibody.

12.2 CYTOTOXICITY ASSAY USING THE ANTIBODY-HEMATOPORPHYRIN DIHYDRAZIDE CONJUGATE

In vitro cytotoxicity assays were carried out in 96 well U-bottom Costar tissue culture plates (Costar, Cambridge, Mass.). The target cells (MOLT-4, ATCC CRL 1582), were obtained from American Type Culture Collection, Rockville, Md. as were control cells (Raji, ATCC CCL 86). The MOLT-4 cell line is a T-cell line derived from the human peripheral blood of a patient with acute lymphoblastic leukemia. The Raji cell line is a lymphoblastic-like cell line derived from a patient with Burkitt's lymphoma. The cells were washed 2 times with RPMI 1640 culture medium (10% Fetal Calf Serum, 2% Glutamine, 1% Penicillin-Streptomyocin) (M. A. Bioproducts, Walkersville, Md.) and diluted to a concentration of 106 cells/ml. The CYT-021 antibody-hematoporhyrin dihydrazide conjugate was filtered through a 0.45 micron syringe filter (Gelman, Ann Arbor, Mich.) and 1:10 dilutions of the conjugate were prepared.

One ml of cells were mixed with 1 ml of the conjugate or appropriate controls and were incubated in the dark for 2 hours in a humidified 37° C., 5% $CO_2$ incubator. The cells were washed three times with RPMI 1640 culture medium (maintaining dark conditions) and the pellets resuspended in RPMI 1640 medium. Aliquots of $10^4$ or $10^5$ cells (see Table IX) (in a volume of 100 ul) were plated in triplicate on each microtiter plate and duplicate plates were prepared. One set of microtiter plates were incubated in the dark for 24 hours as described above. The other set of microtiter plates was then incubated overnight as above while exposed to a standard fluorescent light source.

Viability of cells was then determined by measuring $^3$H-thymidine (New England Nuclear, Boston, Mass.) uptake. The microtiter plates were centrifuged in a TJ-6 centrifuge (Beckman Instruments, Palo Alto, Calif.) for 5 minutes at 1500 rpm. The supernatants were removed and 100 ul of RPMI culture medium containing 1 uCi of $^3$H-thymidine (New England Nuclear, Boston, Mass.) was added to each well. The cells were incubated for at least 4 hours in the $CO_2$ incubator before harvesting onto filter paper using a MASH (Skatron Inc., Sterling, Va.). The filter paper was dissolved in 3 ml Aquasol-2

(New England Nuclear, Boston, Mass.) and counted on a LKB 1212 liquid scintillation counter.

TABLE IX

CYTOTOXICITY OF ANTIBODY-HEMATOPORHYRIN DIHYDRAZIDE CONJUGATE (Ab—Hd)

| Cell Type | Ab—Hd mg/ml | % Cell Killing Dark | % Cell Killing Light |
|---|---|---|---|
| Molt-4 | 0 | 0 | 0 |
|  | 0.05 | 15 | 99 |
|  | 0.005 | 14 | 95 |
| Raji | 0 | 0 | 3 |
|  | 0.05 | 0 | 7 |

As illustrated in Table IX, the present of killing of target cells incubated with the Ab-Hd conjugate and exposed to light was close to 100 percent. Control cells incubated with the CYT-021 Antibody-hemotoporphyrin-dihydrazide conjugate and kept in the dark incorporated maximum amounts of $^3$H-thymidine and no significant mortality was observed.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for preparing a pharmaceutical antibody-therapeutic agent conjugate composition suitable for in vivo administration and for the in vivo delivery of a therapeutic agent, comprising:
    (a) reacting an antibody or antibody fragment with an oxidizing agent to form an aldehyde group in a carbohydrate moiety of the antibody or antibody fragment in which the carbohydrate moiety is located outside the antigen binding region of the antibody or antibody fragment;
    (b) reacting the aldehyde group of the resultant oxidized carbohydrate moiety of the antibody or antibody fragment with an amine group of a therapeutic agent containing an amine group selected from the group consisting of primary amine, secondary amine, hydrazine, hydrazide, hydroxylamine, phenylhydrazine, semicarbazide and thio-semicarbazide groups, to form a soluble antibody-therapeutic agent conjugate characterized by (i) substantially the same immunospecificity as the unconjugated antibody or antibody fragment; and (ii) aqueous solubility such that the antibody-therapeutic agent conjugate is suitable for in vivo administration and
    (c) combining a therapeutically effective amount of the soluble antibody-therapeutic agent conjugate with a pharmaceutical carrier.

2. The method according to claim 1, wherein the oxidizing agent is an enzyme.

3. The method according to claim 1, wherein the oxidizing agent is an oxygen acid.

4. The method according to claim 1, wherein the antibody fragment is selected from the group consisting of Fab fragments, (Fab')$_2$ fragments and half antibody molecules.

5. The method according to claim 1, wherein the antibody or antibody fragment is a monoclonal antibody or a monoclonal antibody fragment.

6. The method according to claim 1, wherein the antibody-therapeutic agent conjugate is stabilized by exposure to an effective amount of a reducing agent.

7. A method for preparing a pharmaceutical antibody-therapeutic agent conjugate composition suitable for in vivo administration and for the in vivo delivery of a therapeutic agent, comprising:
    (a) reacting an antibody or antibody fragment with an oxidizing agent to form an aldehyde group in a carbohydrate moiety of the antibody or antibody fragment, in which the carbohydrate moiety is located outside the antigen binding region of the antibody or antibody fragment;
    (b) reacting the aldehyde group of the resultant oxidized carbohydrate moiety of the antibody or antibody fragment with an amine group of the linker portion of a linker-therapeutic agent intermediate comprising a linker portion, containing an amine group selected from the group consisting of primary amine, secondary amine, hydrazine, hydrazide, hydroxylamine, phenylhydrazine, semicarbazide and thiosemicarbazide groups, covalently attached to a therapeutic agent, to form a soluble antibody-therapeutic agent conjugate characterized by (i) substantially the same immunospecificity as the unconjugated antibody or antibody fragment; and (ii) aqueous solubility such that the antibody-therapeutic agent conjugate is suitable for in vivo administration; and
    (c) combining a therapeutically effective amount of the soluble antibody-therapeutic agent conjugate with a pharmaceutical carrier.

8. The method according to claim 7, wherein the oxidizing agent is an enzyme.

9. The method according to claim 7, wherein the oxidizing agent is an oxygen acid.

10. The method according to claim 7, wherein the antibody fragment is selected from the group consisting of Fab fragments, (Fab')$_2$ fragments and half antibody molecules.

11. The method according to claim 7, wherein the antibody or antibody fragment is a monoclonal antibody or a monoclonal antibody fragment.

12. The method according to claim 7, wherein the antibody-therapeutic agent conjugate is stabilized by exposure to an effective amount of a reducing agent.

13. The method according to claim 7, wherein the linker is a branched linker.

14. The method according to claim 7, wherein the linker is susceptible to cleavage by activated complement.

15. The method according to claim 7, wherein the linker is susceptible to cleavage by an enzyme having proteolytic activity.

16. A method for preparing a pharmaceutical antibody-therapeutic agent conjugate composition suitable for in vivo administration and for the in vivo delivery of a therapeutic agent, comprising: covalently attaching the linker portion of an antibody-linker intermediate comprising a linker portion covalently attached to an oxidized carbohydrate moiety of an antibody or antibody fragment, in which the carbohydrate moiety is located outside the antigen binding region of the antibody or antibody fragment, to a therapeutic agent to form a soluble antibody-therapeutic agent conjugate characterized by (a) substantially the same immunospecificity as the unconjugated antibody or antibody fragment; (b) aqueous solubility such that the antibody-therapeutic agent conjugate is suitable for in vivo administration, and combining a therapeutically effective amount of the soluble antibody-therapeutic agent conjugate with a pharmaceutical carrier.

17. The method according to claim 16, wherein the antibody fragment is selected from the group consisting of Fab fragments, (Fab')$_2$ fragments and half antibody molecules.

18. The method according to claim 16, wherein the antibody or antibody fragment is a monoclonal antibody or a monoclonal antibody fragment.

19. The method according to claim 16, wherein the antibody-linker intermediate is stabilized by exposure to an effective amount of a reducing agent.

20. The method according to claim 16, wherein the linker is a branched linker.

21. The method according to claim 16, wherein the linker is susceptible to cleavage by activated complement.

22. The method according to claim 16, wherein the linker is susceptible to cleavage by an enzyme having proteolytic activity.

23. A method for preparing a pharmaceutical antibody-therapeutic agent conjugate composition suitable for in vivo administration and for the in vivo delivery of a therapeutic agent, comprising:
   (a) reacting an antibody or antibody fragment with an oxidizing agent to form an aldehyde group in a carbohydrate moiety of the antibody or antibody fragment, in which the carbohydrate moiety is located outside the antigen binding region of the antibody or antibody fragment;
   (b) reacting the aldehyde group of the resultant oxidized carbohydrate moiety of the antibody or antibody fragment with an amine group of a linker containing an amine group selected from the group consisting of primary amine, secondary amine, hydrazine, hydrazide hydroxylamine, phenylhydrazine, semicarbazide and thiosemicarbazide groups, to form an antibody-linker intermediate having substantially the same immunospecificity as the unconjugated antibody or antibody fragment;
   (c) covalently attaching the linker portion of the antibody-linker intermediate to a therapeutic agent to form a soluble antibody-therapeutic agent conjugated in which the antibody-therapeutic conjugate is characterized by (i) substantially the same immunospecificity as the unconjugated antibody or antibody fragment; and (ii) aqueous solubility such that the antibody-therapeutic agent conjugate is suitable for in vivo administration; and
   (d) combining a therapeutically effective amount of the soluble antibody-therapeutic agent conjugate with a pharmaceutical carrier.

24. The method according to claim 23, wherein the oxidizing agent is an enzyme.

25. The method according to claim 23, wherein the oxidizing agent is an oxygen acid.

26. The method according to claim 23, wherein the antibody fragment is selected from the group consisting of Fab fragments, (Fab')$_2$ fragments and half antibody molecules.

27. The method according to claim 23, wherein the antibody or antibody fragment is a monoclonal antibody or a monoclonal antibody fragment.

28. The method according to claim 23, wherein the antibody-linker intermediate is stabilized by exposure to an effective amount of a reducing agent.

29. The method according to claim 23, wherein the linker is a branched linker.

30. The method according to claim 23, wherein the linker is susceptible to cleavage by activated complement.

31. The method according to claim 23, wherein the linker is susceptible to cleavage by an enzyme having proteolytic activity.

32. A method for preparing a pharmaceutical antibody-therapeutic agent conjugate composition suitable for in vivo administration and for the in vivo delivery of a therapeutic agent, comprising:
   (a) reacting an antibody or antibody fragment with an oxidizing agent to form an aldehyde group in a carbohydrate moiety of the antibody or antibody fragment, in which the carbohydrate moiety is located outside the antigen binding region of the antibody or antibody fragment;
   (b) reacting the aldehyde group of the resultant oxidized carbohydrate moiety of the antibody or antibody fragment with an amine group of a spacer portion of a linker, said linker comprising a spacer element covalently attached to a cleavable element and said spacer element containing an amine group selected from the group consisting of primary amine, secondary amine, hydrazine, hydrazide, hydroxylamine, phenylhydrazine, semicarbazide and thiosemicarbazide groups, to form an antibody-linker intermediate having substantially the same immunospecificity as the unconjugated antibody or antibody fragment;
   (c) covalently attaching the cleavable element of the antibody-linker intermediate to a therapeutic agent to form a soluble antibody-therapeutic agent conjugate in which the antibody-therapeutic conjugate is characterized by (i) substantially the same immunospecificity as the unconjugated antibody or antibody fragment; (ii) aqueous solubility such that the antibody-therapeutic agent conjugate is suitable for in vivo administration; and
   (d) combining a therapeutically effective amount of the soluble antibody-therapeutic agent conjugate with a pharmaceutical carrier.

33. The method according to claim 32, wherein the oxidizing agent is an enzyme.

34. The method according to claim 32, wherein the oxidizing agent is an oxygen acid.

35. The method according to claim 32, wherein the antibody fragment is selected from the group consisting of Fab fragments, (Fab')$_2$ fragments and half antibody molecules.

36. The method according to claim 32, wherein the antibody or antibody fragment is a monoclonal antibody or a monoclonal antibody fragment.

37. The method according to claim 32, wherein the antibody-linker intermediate is stabilized by exposure to an effective amount of a reducing agent.

38. The method according to claim 32, wherein the linker is a branched linker.

39. The method according to claim 32, wherein the cleavable element is susceptible to cleavage by activated complement.

40. The method according to claim 32, wherein the cleavable element is susceptible to cleavage by an enzyme having proteolytic activity.

41. A method for preparing a pharmaceutical antibody-therapeutic agent conjugate composition suitable for in vivo administration and for the in vivo delivery of a therapeutic agent, comprising:

(a) reacting an antibody or antibody fragment with an oxidizing agent to form an aldehyde group in a carbohydrate moiety of the antibody or antibody fragment, in which the carbohydrate moiety is located outside the antigen binding region of the antibody or antibody fragment; and (b) reacting the aldehyde group of the resultant oxidized carbohydrate moiety of the antibody or antibody fragment with an amine group of a linker-therapeutic agent intermediate, said linker-therapeutic agent intermediate comprising a spacer element covalently attached to a cleavable element which is covalently attached to a therapeutic agent, and said amine group located on said spacer element and selected from the group consisting of primary amine, secondary amine, hydrazine, hydrazide, hydroxylamine, phenylhydrazine, semicarbazide and thiosemicarbazide groups, to form a soluble antibody-therapeutic agent conjugate characterized by (i) substantially the same immunospecificity as the unconjugated antibody or antibody fragment; and (ii) aqueous solubility such that the antibody-therapeutic agent conjugate is suitable for in vivo administration; and (c) combining a therapeutically effective amount of the soluble antibody-therapeutic agent conjugate with a pharmaceutical carrier.

42. The method according to claim 30, wherein the oxidizing agent is an enzyme.

43. The method according to claim 41, wherein the oxidizing agent is an oxygen acid.

44. The method according to claim 41, wherein the antibody fragment is selected from the group consisting of Fab fragments, (Fab')$_2$ fragments and half antibody molecules.

45. The method according to claim 41, wherein the antibody or antibody fragment is monoclonal antibody or a monoclonal antibody fragment.

46. The method according to claim 41, wherein the antibody-therapeutic agent conjugate is stabilized by exposure to an effective amount of a reducing agent.

47. The method according to claim 41, wherein the linker is a branched linker.

48. The method according to claim 41, wherein the cleavable element is susceptible to cleavage by activated complement.

49. The method according to claim 41, wherein the cleavable element is susceptible to cleavage by an enzyme having proteolytic activity.

50. A method for preparing a pharmaceutical antibody-therapeutic agent conjugate composition suitable for in vivo administration and for the in vivo delivery of a therapeutic agent, comprising:

(a) reacting an antibody or antibody fragment with an oxidizing agent to form an aldehyde group in a carbohydrate moiety of the antibody or antibody fragment, in which the carbohydrate moiety is located outside the antigen binding region of the antibody or antibody fragment;

(b) reacting the aldehyde group of the resultant oxidized carbohydrate moiety of the antibody or antibody fragment with a spacer element containing an amine group selected from the group consisting of primary amine, secondary amine, hydrazine, hydrazide, hydroxylamine, phenylhydrazine, semicarbazide and thiosemicarbazide groups, to form an antibody-spacer element intermediate having substantially the same immunospecificity as the unconjugated antibody or antibody fragment;

(c) covalently attaching the spacer element of the antibody-spacer element intermediate to a cleavable element of a cleavalbe element-therapeutic agent intermediate, to form a soluble antibody-therapeutic agent conjugate in which the antibody-therapeutic conjugate is characterized by (i) substantially the same immunospecificity as the unconjugated antibody or antibody fragment; and (ii) aqueous solubility such that the antibody-therapeutic agent conjugate is suitable for in vivo administration; and (d) combining a therapeutically effective amount of the soluble antibody-therapeutic agent conjugate with a pharmaceutical carrier.

51. The method according to claim 50, wherein the oxidizing agent is an enzyme.

52. The method according to claim 50, wherein the oxidizing agent is an oxygen acid.

53. The method according to claim 50, wherein the antibody fragment is selected from the group consisting of Fab fragments, (Fab')$_2$ fragments and half antibody molecules.

54. The method according to claim 50, wherein the antibody or antibody fragment is a monoclonal antibody or a monoclonal antibody fragment.

55. The method according to claim 50, wherein the antibody-spacer element intermediate is stabilized by exposure to an effective amount of a reducing agent.

56. The method according to claim 50, wherein the spacer element is a branched spacer element.

57. The method according to claim 50, wherein the cleavable element is susceptible to cleavage by activated complement.

58. The method according to claim 50, wherein the cleavable element is susceptible to cleavage by an enzyme having proteolytic activity.

59. A method for preparing a pharmaceutical antibody-therapeutic agent conjugate, composition suitable for in vivo administration and for the in vivo delivery of a therapeutic agent, comprising:

(a) reacting an antibody or antibody conjugate with an oxidizing agent to form an aldehyde group in a carbohydrate moiety of the antibody or antibody fragment, in which the carbohydrate moiety is located outside the antigen binding region of the antibody or antibody fragment;

(b) reacting the aldehyde group of the resultant oxidized carbohydrate moiety of the antibody or antibody fragment with a spacer element containing an amine group selected from the group consisting of primary amine, secondary amine, hydrazine, hydrazide, hydroxylamine, phenylhydrazine, semicarbazide and thiosemicarbazide groups, to form an antibody-spacer element intermediate having substantially the same immunospecificity as the unconjugated antibody or antibody fragment;

(c) covalently attaching the spacer element of the antibody-spacer element intermediate to a cleavable element to form an antibody-spacer element-cleavable element intermediate;

(d) covalently attaching the cleavable element of the antibody-spacer element-cleavable element intermediate to a therapeutic agent to form a soluble antibody-therapeutic agent conjugate in which the antibody-therapeutic conjugate is characterized by (i) substantially the same immunospecificity as the unconjugated antibody or antibody fragment; and (ii) aqueous solubility such that the antibody-therapeutic agent conjugate is suitable for in vivo administration; and (e) combining a therapeutically effective amount of the soluble antibody-therapeutic agent conjugate with a pharmaceutical carrier.

60. The method according to claim 59, wherein the oxidizing agent is an enzyme.

61. The method according to claim 59, wherein the oxidizing agent is an oxygen acid.

62. The method according to claim 59, wherein the antibody fragment is selected from the group consisting of Fab fragments, (Fab')$_2$ fragments and half antibody molecules.

63. The method according to claim 59, wherein the antibody or antibody fragment is a monoclonal antibody or a monoclonal antibody fragment.

64. The method according to claim 59, wherein the antibody-spacer element intermediate is stabilized by exposure to an effective amount of a reducing agent.

65. The method according to claim 59, wherein the spacer element is a branched spacer element.

66. The method according to claim 59, wherein the cleavable element is susceptible to cleavage by activated complement.

67. The method according to claim 59, wherein the cleavable element is susceptible to cleavage by an enzyme having proteolytic activity.

68. A pharmaceutical composition suitable for in vivo administration and for the in vivo delivery of a therapeutic agent, comprising: a therapeutically effective amount of an antibody-therapeutic agent conjugate in which: a therapeutic agent is attached via a covalent bond to an oxidized carbohydrate moiety outside the antigen binding region of an antibody or antibody fragment to form a soluble antibody-therapeutic agent conjugate characterized by (a) substantially the same immunospecificity as the unconjugated antibody or antibody fragment; and (b) aqueous solubility such that the antibody-therapeutic agent conjugate is suitable for in vivo administration and a pharmaceutical carrier.

69. The pharmaceutical composition according to claim 68, wherein the covalent bond is an imine, enamine, hydrazone, oxime, phenylhydrazone, semicarbazone, thiosemicarbazone, or a reduced form thereof.

70. The pharmaceutical composition according to claim 68, wherein the antibody fragment is selected from the group consisting of Fab fragments, (Fab')$_2$ fragments and half antibody molecules.

71. The pharmaceutical composition according to claim 68, wherein the antibody or antibody fragment is a monoclonal antibody or a monoclonal antibody fragment.

72. A pharmaceutical composition suitable for in vivo administration and for the in vivo delivery of a therapeutic agent, comprising: a therapeutically effective amount of an antibody-therapeutic agent conjugate in which: a therapeutic agent is attached via a covalent bond to a linker which is covalently attached to an oxidized carbohydrate moiety outside the antigen binding region of an antibody or antibody fragment to form a soluble antibody-therapeutic agent conjugate characterized by (a) substantially the same immunospecificity as the unconjugated antibody or antibody fragment; and (b) aqueous solubility such that the antibody-therapeutic agent conjugate is suitable for in vivo administration and a pharmaceutical carrier.

73. The pharmaceutical composition according to claim 72, wherein the covalent bond is an imine, enamine, hydrazone, oxime, phenylhydrazone, semicarbazone, thiosemicarbazone, or a reduced form thereof.

74. The pharmaceutical composition according to claim 72, wherein the antibody fragment is selected from the group consisting of Fab fragments, (Fab')$_2$ fragments and half antibody molecules.

75. The pharmaceutical composition according to claim 72, wherein the antibody or antibody fragment is a monoclonal antibody or a monoclonal antibody fragment.

76. The pharmaceutical composition according to claim 72, wherein the linker is a branched linker.

77. The pharmaceutical composition according to claim 72, wherein the linker comprises a spacer element and a cleavable element.

78. The pharmaceutical composition according to claim 77, wherein the cleavable element is susceptible to cleavage to complement.

79. The pharmaceutical composition according to claim 77, wherein the cleavable element is susceptible to cleavage by an enzyme having proteolytic activity.

* * * * *

UNITED STATES PATENT AND TRADEMARK OFFICE
CERTIFICATE OF CORRECTION

PATENT NO. : 4,867,973

DATED : September 19, 1989

INVENTOR(S) : Rodwell et al.

It is certified that error appears in the above-identified patent and that said Letters Patent is hereby corrected as shown below:

ON TITLE PAGE:

[75] Inventors should read only: John D. Rodwell and Thomas J. McKearn

Column 5, line 40, "hepatatoma" should read --hepatoma--; line 45, "therepeutic" should read --therapeutic--.

Column 8, line 2, "therepeutic" should read --therapeutic--; line 66, "form" should read --from--.

Column 17, line 56, "immunoglubulin" should read --immunoglobulin--.

Column 20, line 53, "dihyddrazide" should read --dihydrazide--.

Column 28, line 65, "i" should read --in--; line 66, "e" --be--.

Column 29, line 27, "5.5" should read --5.6--; line 41, "complement linker" should read --complement. If the linker--.

UNITED STATES PATENT AND TRADEMARK OFFICE
CERTIFICATE OF CORRECTION

PATENT NO. : 4,867,973   Page 2 of 3

DATED : September 19, 1989

INVENTOR(S) : Rodwell and McKearn

It is certified that error appears in the above-identified patent and that said Letters Patent is hereby corrected as shown below:

Column 30, line 48, "ATTACHMENT" should read --6.2 ATTACHMENT--; line 55, "iobutylchloroformate" should read --isobutylchloroformate--.

Column 35, line 60, "2X108" should read --$2 \times 10^8$--.

Column 36, line 6, "be" should be --by--; line 12, "an" should read --and--; line 36, "00 ul" should read --200 ul--; and line 37, "2X108" should read --$2 \times 10^8$--.

Column 39, lines 43, 52 and in the formula, first occurrence, "Tyr" should read --Tyr*--.

Column 40, line 33, "Tyr" should read --Tyr*--.

Column 41, line 34, "151-" should read --1151--; line 54, "(NaCNBH3)" should read --(NaCNBH$_3$)--.

Column 42, line 55, "results" should read --The--.

UNITED STATES PATENT AND TRADEMARK OFFICE
CERTIFICATE OF CORRECTION

PATENT NO. : 4,867,973

DATED : September 19, 1989

INVENTOR(S) : Rodwell and McKearn

It is certified that error appears in the above-identified patent and that said Letters Patent is hereby corrected as shown below:

Column 43, line 15, "-GLY-GLY" should read ---GLY-GLY-ARG-TYR*--; line 49, "1X109" should read --1 x $10^9$--.

Column 46, line 11, "a ml" should read -- a 10 ml--; line 14, "a solution" should read --a 10% solution--; and line 40, "106" should read --$10^6$--.

Column 51, claim 42, "30" should read --41--.

Column 52, claim 50, line 8, "cleavalbe" should read --cleavable--.

Signed and Sealed this

Twenty-fifth Day of February, 1992

Attest:

HARRY F. MANBECK, JR.

*Attesting Officer*     *Commissioner of Patents and Trademarks*